(12) United States Patent
De Lombaert et al.

(10) Patent No.: US 6,423,727 B1
(45) Date of Patent: Jul. 23, 2002

(54) CERTAIN THIOL INHIBITORS OF ENDOTHELIN-CONVERTING ENZYME

(75) Inventors: Stéphane De Lombaert, Madison, CT (US); Cynthia Anne Fink, Lebanon, NJ (US); Fariborz Firooznia, Eastchester, NY (US); Denton Wade Hoyer, Dexter, MI (US); Arco Yingcheu Jeng, Piscataway, NJ (US)

(73) Assignee: Novartis AG, Basel (CH)

( * ) Notice: Subject to any disclaimer, the term of this patent is extended or adjusted under 35 U.S.C. 154(b) by 31 days.

(21) Appl. No.: 09/690,060

(22) Filed: Oct. 16, 2000

Related U.S. Application Data

(63) Continuation of application No. PCT/EP99/02690, filed on Apr. 21, 1999.
(60) Provisional application No. 60/150,684, filed on Apr. 23, 1998.

(51) Int. Cl.$^7$ ................................................. A01N 43/40
(52) U.S. Cl. .................. 514/354; 514/530; 514/531; 514/332; 514/538; 562/424; 562/427; 562/503
(58) Field of Search ................. 514/530, 531, 514/332, 354, 538, 539, 542; 562/424, 427, 503

(56) References Cited

U.S. PATENT DOCUMENTS

| | | | | |
|---|---|---|---|---|
| 5,432,186 A | * | 7/1995 | Fink | |
| 5,506,244 A | * | 4/1996 | Fink | |
| 5,508,266 A | | 4/1996 | Fink | |
| 5,550,119 A | * | 8/1996 | De Lombaert et al. | |
| 5,668,158 A | * | 9/1997 | Fink | |

FOREIGN PATENT DOCUMENTS

| | | |
|---|---|---|
| EP | 655 461 A | 5/1995 |
| WO | WO 95 12611 | 5/1995 |
| WO | WO 97/32849 | 9/1997 |
| WO | WO 97/32874 | 9/1997 |
| WO | WO 99/55723 | 11/1999 |
| WO | WO 99/55726 | 11/1999 |

OTHER PUBLICATIONS

Kukkola et al, Journal of Cardiovascular Pharmacology, 26(suppl.3, s65–s67, 1995.*
McKittrick et al, Bioorganic and Medicinal Chemistry Letters, 6 (14), 1629–1634, 1996.*
Bioorganic Med. Chem., vol. 6, (19), pp. 2317–2322 (1996).
Bioorganic Med. Chem., vol. 6, (14) pp. 1629–1634 (1996).
Derwent Abstract of WO 97/32874.
Fink, E.A., J. Med. Chem., vol. 38, pp. 5023–5030 (1995).
Tetrahedron Letters, vol. 38, pp. 7645–7648 (1997).
Deprez P. et al., Biorganic & Medicinal Chemistry Letters, vol. 6, No. 19, pp. 2317–2322 (1996).
Balwierczak J.L. et al., Biochemical Pharmacology, vol. 49, No. 3, pp. 291–296 (1995).
Fink E.A., Journal of Medicinal Chemistry, vol. 39, No. 16, pp. 3158–3168 (1996).
Kukkola P.J. et al., Journal of Cardiovascular Pharmacology, vol. 26, No. SUPPL. 03, pp. 565–568 (1995).

* cited by examiner

*Primary Examiner*—Gary Geist
*Assistant Examiner*—Hector M Reyes
(74) *Attorney, Agent, or Firm*—Norbert Gruenfeld

(57) ABSTRACT

Disclosed as endothelin converting enzyme inhibitors are the compounds of the formula

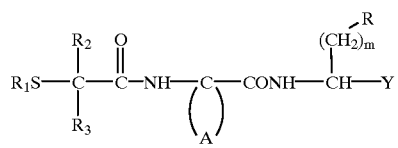

(I)

wherein the variables have the meanings as defined hereinbefore.

17 Claims, No Drawings

CERTAIN THIOL INHIBITORS OF ENDOTHELIN-CONVERTING ENZYME

This application is a continuation application of International application No. PCT/EP99/02690 filed Apr. 21, 1999 (designating the United States) which, in turn, claims the benefit of U.S. application Ser. No. 09/065,265 filed Apr. 23, 1998, which was converted to provisional application No. 60/150,684, said documents being incorporated herein by reference.

The present invention relates to the compounds of formula I below which have been discovered to be useful as endothelin-converting enzyme (ECE) inhibitors in mammals.

The thiol derivatives described herein inhibit the formation of endothelin, reduce the plasma and tissue levels of endothelin and inhibit the biological effects of endothelin activity in mammals.

The present invention provides a method of inhibiting ECE and a method of treating and/or preventing endothelin dependent conditions and diseases, e.g. cardio- and cerebrovascular disorders such as essential hypertension, vasoconstriction, congestive heart failure, pulmonary hypertension, cerebral ischemia-(stroke), subarachnoid hemorrhage, traumatic brain injury, acute and chronic renal failure, atherosclerosis, cerebral vasospasm, arterial hypertrophy, restenosis, Raynaud's disease, myocardial infarction, obesity; also respiratory disorders such as bronchial asthma; gastrointestinal disorders such as inflammatory bowel disease, pancreatitis, emesis; also prostate hyperplasia, migraine, diabetes mellitus (diabetic nephropathy), preeclampsia, glaucoma and transplantation rejection, such as in aorta or solid organ transplantation in either allo- or xeno- transplantation; as well as erectile dysfunction; using the compounds described below.

The present invention is also directed to ECE inhibiting pharmaceutical compositions and to novel compounds disclosed herein.

Certain compounds for which the new ECE inhibiting use has been discovered have been disclosed in U.S. Pat. No. 5,506,244 (which is incorporated herein by reference) as angiotensin converting enzyme and neutral endopeptidase inhibitors. Compounds of formula III below wherein Y represents carboxyl or esterified carboxyl, R is 4-biphenylyl, 3-indolyl or 5-hydroxy-3-indolyl, and $R_2$ is isopropyl, are examples in said patent.

The present invention relates to the inhibition of endothelin converting enzyme using a thiol derivative of formula I

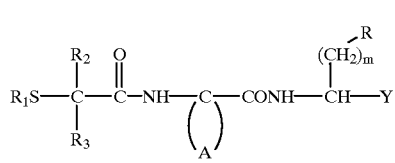

(I)

wherein

R represents bicyclic carbocyclic aryl or bicyclic heterocyclic aryl; or a wholly or partially saturated form thereof; or R represents monocyclic carbocyclic aryl substituted by carbocyclic aryl or by heterocyclic aryl; or R represents monocyclic carbocyclic aryl substituted by cycloalkyl; or R represents monocyclic carbocyclic aryl substituted by azacycloalkyl which is optionally substituted by lower alkyl or acyl; or R represents cycloalkyl substituted by cycloalkyl or azacycloalkyl;

$R_1$ represents hydrogen or acyl;

$R_2$ represents hydrogen, lower alkyl, carbocyclic or heterocyclic aryl, carbocyclic or heterocyclic aryl-lower alkyl, cycloalkyl, cycloalkyl-lower alkyl, biaryl, biaryl-lower alkyl, (hydroxy, lower alkoxy or acyloxy)-lower alkyl, or lower alkyl-(thio, sulfinyl or sulfonyl)-lower alkyl;

$R_3$ represents hydrogen or lower alkyl; or $R_2$ and $R_3$ together with the carbon atom to which they are attached represent cycloalkylidene or benzo-fused cycloalkylidene;

A together with the carbon atom to which it is attached forms a ring and represents 3 to 10 membered cycloalkylidene or 5 to 10 membered cycloalkenylidene radical which may be substituted by lower alkyl or aryl-lower alkyl or may be fused to a saturated or unsaturated carbocyclic 5–7-membered ring; or A together with the carbon to which it is attached represents 5 to 6 membered oxacycloalkylidene, thiacycloalkylidene or azacycloalkylidene optionally substituted by lower alkyl, acyl or aryl-lower alkyl; or A together with the carbon atom to which it is attached represents 2,2-norbornylidene;

m is zero or 1–3;

Y represents 5-tetrazolyl, carboxyl or carboxyl derivatized in form of a pharmaceutically acceptable ester;

disulfide derivatives derived from said compounds wherein $R_1$ is hydrogen; or a pharmaceutically acceptable salts thereof; pharmaceutical compositions comprising said compounds; methods for preparation of said compounds; intermediates; and methods of treating disorders in mammals which are responsive to ECE inhibition by administration of said compounds to mammals in need of such treatment.

Pharmaceutically acceptable esters are preferably prodrug ester derivatives, such being convertible by solvolysis or under physiological conditions to the free carboxylic acids of formula I.

Encompassed by the instant invention are any prodrug derivatives of compounds of the invention having a free carboxyl, sulfhydryl or hydroxyl group, said prodrug derivatives being convertible by solvolysis or under physiological conditions to the free carboxyl, sulfhydryl and/or hydroxyl compounds. Prodrug derivatives are e.g. the esters of free carboxylic acids and S-acyl and O-acyl derivatives of thiols, or alcohols, wherein acyl has meaning as defined herein.

Pharmaceutically acceptable prodrug esters of carboxylic acids are preferably e.g. lower alkyl esters, cycloalkyl esters, lower alkenyl esters, aryl-lower alkyl esters, α-(lower alkanoyloxy)-lower alkyl esters such as the pivaloyloxymethyl ester, and α-(lower alkoxycarbonyl- or di-lower alkylamino carbonyl-)-lower alkyl esters.

Pharmaceutically acceptable salts are salts derived from pharmaceutically acceptable bases for any acidic compounds of the invention, e.g. those wherein Y represents carboxyl. Such are e.g. alkali metal salts (e.g. sodium, potassium salts), alkaline earth metal salts (e.g. magnesium, calcium salts), amine salts (e.g. tromethamine salts).

Compounds of formula I, depending on the nature of substituents, possess one or more asymmetric carbon atoms. The resulting diastereomers and optical antipodes are encompassed by the instant invention. Preferred is the configuration wherein the asymmetric carbon with the substituent Y has the S-configuration.

Preferred as endothelin converting enzyme inhibitors are the compounds with the S-configuration of formula II

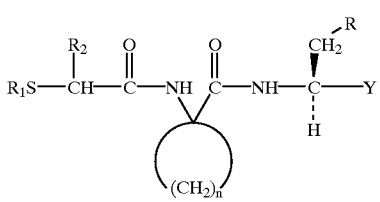

(II)

wherein R represents benzothiophenyl, naphthyl, benzofuranyl, indolyl, or monocyclic carbocyclic aryl substituted by monocyclic carbocyclic aryl or by monocyclic heterocyclic aryl; $R_1$ represents hydrogen or carboxyl derived acyl; $R_2$ represents lower alkyl, hydroxy-lower alkyl, (lower alkylthio- or lower alkoxy-)lower alkyl, carbocyclic or heterocyclic aryl, carbocyclic or heterocyclic aryl-lower alkyl, cycloalkyl, cycloalkyl-lower alkyl, or biaryl-lower alkyl; Y represents 5-tetrazolyl, carboxyl or carboxyl derivatized in form of a pharmaceutically acceptable ester; n represents 2–6, preferably 2, 4 or 5; disulfide derivatives derived from said compounds wherein $R_1$ is hydrogen; or a pharmaceutically acceptable salt thereof.

Further preferred are said compounds of formula II wherein R has meaning as defined above; $R_1$ represents hydrogen, aryl-lower alkanoyl, lower alkanoyl, lower alkoxy-lower alkanoyl, or heterocyclic or carbocyclic aroyl; $R_2$ represents $C_2$–$C_4$ alkyl interrupted by S or O, $C_2$–$C_5$-alkyl or cyclohexyl; Y represents 5-tetrazolyl, carboxyl, lower alkoxycarbonyl, carbocyclic or heterocyclic aryl-lower alkoxycarbonyl, α-(lower alkanoyloxy-, lower alkoxycarbonyl- or di-lower alkylaminocarbonyl-)lower alkoxycarbonyl; n is 2, 4 or 5; or a pharmaceutically acceptable salt thereof.

Particularly preferred as endothelin converting enzyme inhibitors are said compounds with the S-configuration of formula III

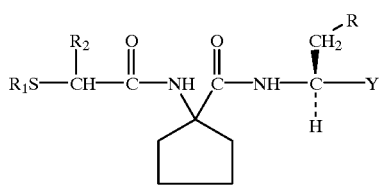

(III)

and of formula IIIa

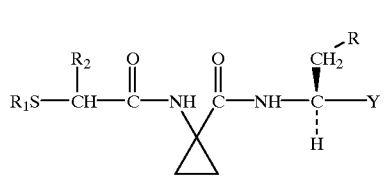

(IIIa)

wherein
R represents benzothiophenyl, naphthyl, benzofuranyl, indolyl, or monocyclic carbocyclic aryl substituted by monocyclic carbocyclic aryl or by monocyclic heterocyclic aryl;
$R_1$ represents hydrogen, lower alkanoyl, methoxy-lower alkanoyl, benzoyl or pyridylcarbonyl;
$R_2$ represents $C_2$–$C_5$-alkyl, cyclohexyl or $C_2$–$C_4$-alkyl interrupted by O or S;
Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

A further embodiment of the invention relates to the compounds with the S-configuration of formula IIIb

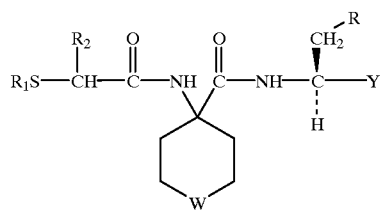

(IIIb)

wherein
R represents benzothiophenyl, naphthyl, benzofuranyl, indolyl or monocarbocyclic aryl substituted by monocyclic carbocyclic aryl or by monocyclic heterocyclic aryl;
W represents $CH_2$, O, S or $NR_4$ in which $R_4$ is hydrogen, acyl, lower alkyl or aryl-lower alkyl;
$R_1$ represents hydrogen, lower alkanoyl, methoxy-lower alkanoyl, benzoyl or pyridylcarbonyl;
$R_2$ represents $C_2$–$C_5$-alkyl, cyclohexyl or $C_2$–$C_4$-alkyl interrupted by O or S;
Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

Further preferred are said compounds of formula II, III, IIIa or IIIb wherein R represents 4-biphenylyl or 3-indolyl; $R_1$ represents hydrogen or lower alkanoyl; $R_2$ represents $C_3$–$C_5$-alkyl, Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

A particular preferred embodiment relates to compounds of any of the above formulae wherein R represents 4-biphenylyl; $R_1$ is hydrogen or lower alkanoyl; $R_2$ is n-propyl, n-butyl or isobutyl; and Y is 5-tetrazolyl or particularly preferred carboxyl or lower alkoxycarbonyl; or a pharmaceutically acceptable salt thereof.

A particular aspect of the invention is directed to the novel compounds of formulae I, II, III, IIIa and IIIb wherein
(a) R represents monocyclic carbocyclic aryl substituted by cycloalkyl;
(b) R represents monocyclic carbocyclic aryl substituted by azacycloalkyl optionally substituted on nitrogen by lower alkyl or acyl;
(c) R represents cycloalkyl substituted by cycloalkyl; and the other symbols have meaning as defined herein.

Another aspect of the invention is directed to the novel compounds of formulae I, II, III, IIIa and IIIb wherein Y represents 5-tetrazolyl and the other symbols have meaning as defined herein.

Preferred compounds of the invention include the novel compounds of formulae III or IIIb wherein Y represents carboxy or lower alkoxycarbonyl; $R_1$ represents hydrogen or lower alkanoyl; $R_2$ represents lower alkyl, lower alkyl substituted by hydroxy, mercapto, phenyl, phenyl substituted by lower alkyl, lower alkoxy, hydroxy, lower alkylthio, halogen, trifluoromethyl, furthermore by phenyl or naphthyl each of which may be unsubstituted or, independently of one another, be substituted by lower alkyl, lower alkoxy, hydroxy, lower alkylthio, halogen or trifluoromethyl, or represents cyclohexyl; and R represents 3-indolyl, 4-(5-isoxazolyl)-phenyl, 4-(2- or 3-pyrrolyl)phenyl, 4-(2- or 3-furanyl)phenyl, 4-(2- or 3-thienyl)phenyl, 4-(2- or 3-pyridyl)-phenyl, piperidin-3-yl-phenyl which is N-unsubstituted or N-substituted by lower alkanoyl, or represents 4-(5-pyrimidinyl)-phenyl, naphthyl, 5,6,7,8-tetrahydro-naphthalen-1-yl, 5,6,7,8-tetryhydro-naphthalen-2-yl or 4-cyclohexyl-phenyl, or represents 4-biphenylyl or 4-biphenylyl substituted on one or both benzene rings by lower alkyl, lower alkoxy, hydroxy, lower alkylthio, halogen or trifluoromethyl; or a pharmaceutically acceptable salt thereof.

Preferred endothelin converting enzyme inhibiting compounds of the invention include alternatively the novel compounds of formula III wherein Y represents 5-tetrazolyl, carboxyl or lower alkoxycarbonyl; $R_1$ represents hydrogen or lower alkanoyl; $R_2$ represents n-propyl, n-butyl, isobutyl, methoxyethyl or methylthioethyl; and R represents 3-indolyl, 4-(5-isoxazolyl)-phenyl, 4-(2- or 3-furanyl) phenyl, 4-(2- or 3-thienyl)phenyl, 4-biphenylyl, 4-(2- or 3-pyridyl)-phenyl, 4-(5-pyrimidinyl)-phenyl, or 4-biphenylyl substituted on one or both benzene rings by lower alkyl, lower alkoxy, hydroxy, lower alkylthio, halogen or trifluoromethyl; or a pharmaceutically acceptable salt thereof.

Particularly preferred are the compounds of formula III wherein (a) Y is carboxyl, $R_1$ is hydrogen, $R_2$ is n-propyl and R is 4-biphenylyl (b) Y is methoxycarbonyl, $R_1$ is acetyl, $R_2$ is n-propyl and R is 4-biphenylyl; and pharmaceutically acceptable salts thereof.

(c) Y is carboxyl, $R_1$ is hydrogen, $R_2$ is isobutyl and R is 3-indolyl; and pharmaceutically acceptable salts thereof.

(d) Y is methoxycarbonyl, $R_2$ is isobutyl and R is 3-indolyl.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, trifluoromethyl, amino, lower alkanoylamino, lower alkyl-(thio, sulfinyl or sulfonyl), lower alkoxycarbonyl, mono- or di-lower alkylcarbamoyl, or mono- or di-lower alkylamino.

Bicyclic carbocyclic aryl represents 1- or 2-naphthyl or 1- or 2-naphthyl preferably substitued by lower alkyl, lower alkoxy or halogen.

Monocyclic heterocyclic aryl represents preferably optionally substituted thiazolyl, thienyl, furanyl, pyridyl, pyrimidinyl, oxazolyl, isoxazolyl, pyrrolyl, imidazolyl, or oxadiazolyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl or hydroxy-lower alkyl.

Optionally substituted thiazolyl represents e.g. 4-thiazolyl, or 4-thiazolyl substituted by lower alkyl.

Optionally substituted pyrimidinyl represents 2-, 4- or 5-pyridridinyl or 2-, 4- or 5-pyrimidinyl preferably substituted by lower alkyl.

Optionally substituted oxazolyl represents 2-, 4- or 5-oxazolyl or 2-, 4- or 5-oxazolyl preferably substituted by lower alkyl.

Optionally substituted isoxazolyl represents 3-, 4- or 5-isoxazolyl or 3-, 4- or 5-isoxazolyl preferably substituted by lower alkyl.

Optionally substituted pyrrolyl represents 1-, 2- or 3-pyrrolyl or 1-, 2- or 3- pyrrolyl preferably substituted by lower alkyl.

Optionally substituted imidazolyl represents 1-, 2- or 4-imidazolyl or 1-, 2- or 4-imidazolyl preferably substituted by lower alkyl.

Optionally substituted oxadiazolyl represents 3- or 5-[1, 2, 4]oxadiazolyl or 3- or 5-[1, 2, 4]oxadiazolyl preferably substituted by lower alkyl.

Bicyclic heterocyclic aryl represents preferably benzothiophenyl, benzofuranyl, indolyl or benzothiazolyl optionally substituted by hydroxy, lower alkyl, lower alkoxy or halogen, advantageously 3-indolyl, 2-benzothiazolyl, 2-benzofuranyl or 3-benzo[b]thiophenyl.

Aryl in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up toand including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

Cycloalkyl represents a saturated cyclic hydrocarbon radical which preferably contains 5 to 7 ring carbons, preferably cyclopentyl or cyclohexyl.

The term cycloalkyl(lower) alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Cycloalkylidene is 3 to 10 membered, preferably 3, 5 or 6-membered, and represents a cycloalkane linking group e.g. cyclopropylidene, cyclopentylidene, cyclohexylidene, cycloheptylidene or cyclooctylidene, in which the two attached groups are attached to the same carbon of the cycloalkane ring.

Cycloalkenylidene is 5 to 10 membered, prefereably 5 or 6-membered, and represents a cycloalkene linking group in which the two attached groups are attached to the same carbon atom of the cycloalkene ring.

Cycloalkylidene fused to a saturated carbocyclic ring represents e.g. perhydronaphthylidene.

Cycloalkylidene fused to an unsaturated carbocyclic ring represents e.g. 1,1- or 2,2-tetralinylidene or 1,1- or 2,2-indanylidene.

5 or 6 Membered oxacycloalkylidene represents preferably a tetrahydrofuran or tetrahydropyran linking group, e.g. tetrahydrofuranylidene or tetrahydropyranylidene, in which the two attached groups are attached to the same carbon atom of the respective rings, e.g. at the 3 or 4 position thereof.

5 or 6 Membered thiacycloalkylidene represents preferably a tetrahydrothiophene or tetrahydrothiopyran linking group in which the two attached groups are attached to the same carbon atom of the respective rings, e.g. at the 3 or 4 position thereof.

5 or 6 Membered azacyloalkylidene represents preferably a pyrrolidine or piperidine linking groups in which the two attached groups are attached to the same carbon atom of the respective rings, e.g. at the 3 or 4 position thereof, and the nitrogen may be substituted by lower alkyl, e.g. methyl, or by aryl-lower alkyl, e.g. benzyl.

Halogen (halo) preferably represents fluoro or chloro, but may also be bromo or iodo.

Acyl is derived from a carboxylic acid and represents preferably optionally substituted lower alkanoyl, cycloalkylcarbonyl, carbocyclic aryl-lower alkanoyl, aroyl, lower alkoxycarbonyl or aryl-lower alkoxycarbonyl, advantageously optionally substituted lower alkanoyl or aroyl.

Lower alkanoyl is preferably acetyl, propionyl, butanoyl, pentanoyl, or pivaloyl.

Optionally substituted lower alkanoyl for example represents lower alkanoyl or lower alkanoyl substituted by lower alkoxycarbonyl, lower alkanoyloxy, lower alkanoylthio, lower alkoxy, or by lower alkylthio; also lower alkanoyl substituted by e.g. hydroxy, di-lower alkylamino, lower alkanoylamino, morpholino, piperidino, pyrrolidino or 1-lower alkylpiperazino.

Aroyl is carbocyclic or heterocyclic aroyl, preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic carbocyclic aryl substituted by carbocyclic aryl is preferably biphenylyl, advantageously 4-biphenylyl, optionally substituted on one or both benzene rings by one or more of lower alkyl, lower alkoxy, hydroxy, lower alkylthio, halogen, trifluoromethyl, amino, acylamino or nitro.

Monocyclic carbocyclic aryl substituted by heterocyclic aryl is preferably phenyl, optionally substituted by lower alkyl, lower alkoxy, hydroxy, lower alkylthio, trifluoromethyl, which is substituted in the para position by monocyclic heterocyclic aryl, preferably optionally substituted thiazolyl, thienyl, furanyl, pyridyl, pyrimidinyl, oxazolyl or isoxazolyl.

Monocyclic heterocyclic aroyl is preferably pyridylcarbonyl or thienylcarbonyl.

Azacycloalkyl represents preferably piperidyl, advantageously 3-piperidyl optionally substituted on nitrogen by lower alkyl or acyl.

Acyloxy is preferably optionally substituted lower alkanoyloxy, lower alkoxycarbonyloxy, monocyclic carbocyclic aroyloxy or monocyclic heterocyclic aroyloxy; also carbocyclic or heterocyclic aryl-lower alkanoyloxy.

Optionally substituted lower alkanoyloxy is preferably lower alkanoyloxy, such as acetyloxy, substituted by any group indicated above under optionally substituted alkanoyl.

Aryl-lower alkoxycarbonyl is preferably monocyclic carbocyclic-lower alkoxycarbonyl, advantageously benzyloxycarbonyl.

Biaryl represents for example 4-biphenylyl.

Biaryl-lower alkyl is preferably 4-biphenylyl-lower alkyl, advantageously 4-biphenylyl-methyl.

The novel compounds of the invention are pharmacologically potent endothelin converting enzyme inhibitors which inhibit the formation of endothelin in mammals. They thus inhibit the biological effects of endothelin in mammals.

The compounds of the invention are thus particularly useful in mammals for the treatment of e.g. hypertension and heart failure, cerebrovascular disorders, e.g. cerebral vasospasm and stroke, acute and chronic renal failure, penile erectile dysfunction, pulmonary disorders e.g. bronchial asthma, and complications associated with organ transplantation.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-5}$ molar and $10^{-9}$ molar concentrations. The dosage in vivo may range depending on the route of administration, between about 0.1 and 50 mg/kg, advantageously between about 1.0 and 25 mg/kg.

The in vitro inhibition of endothelin-converting enzyme can be determined as follows:

The test compound is dissolved in dimethyl sulfoxide or 0.25 M sodium bicarbonate solution, and the solution is diluted with a pH 7.4 buffer to the desired concentration.

Endothelin converting enzyme (ECE) is partially purified from porcine primary aortic endothelial cells by DE52 anion exchange column chromatrography and its activity is quantified by radioimmunoassay as described in Anal. Biochem. 212, 434–436 (1993). Alternatively, the native enzyme can be substituted by a recombinant form of ECE, as described, for example in Cell 78, 473–485 (1994). Human ECE-1 has been described by several groups (Schmidt, M. et al. FEBS Letters, 1994, 356, 238–243; Kaw, S.; Emoto, N.; Jeng, A.; Yanagisawa, M. 4th Int. Conf. on Endothelin; April 23–25, London (UK), 1995; C6; Valdenaire, O. et al. J. Biol. Chem. 1995, 270, 29794–29798; Shimada, K. et al. Biochem. Biophys. Res. Commun., 1995, 207, 807–812). The ECE inhibiton can be determined as described in Biochem. Mol. Biol. Int. 31, (5), 861–867 (1993), by radioimmunoassay to measure ET-1 formed from big ET-1.

Alternatively, recombinant human ECE-1 (rhECE-1) can be used, as follows:

Chinese hamster ovary cells expressing recombinant human endothelin converting enzyme-1 (rhECE-1; Kaw, S.; Emoto, N.; Jeng, A.; Yanagisawa, M. 4th Int. Conf. on Endothelin; April 23–25, London (UK), 1995; C6) are cultured in DMEM/F12 medium containing 10% fetal bovine serum and 1×antibiotic-antimycotic. Cells are harvested by scraping, pelleted by centrifugation, and homogenized at 4° C. in a buffer containing 5 mM $MgCl_2$, 1 $\mu M$ pepstatin A, 100 µM leupeptin, 1 mM PMSF, and 20 mM Tris, pH 7.0, with a ratio of 2 mL of buffer/mL of cells. The cell debris is removed by brief centrifugation, and the supernatant is centrifuged again at 100,000×g for 30 minutes. The resulting pellet is resuspended in a buffer containing 200 mM NaCl and 50 mM Tes, pH 7.0, at a protein concentration about 15 mg/mL and stored in aliquots at −80° C.

To assess the effect of an inhibitor on ECE-1 activity, 10 µg of protein is pre-incubated with the compound at a desired concentration for 20 min at room temperature in 50 mM TES, pH 7.0, and 0.005% Triton X-100 in a volume of 10 µL. Human big ET-1 (5 µL) is then added to a final concentration of 0.2 µM, and the reaciton mixture is further incubated for 2 h at 37° C. The reaction is stopped by adding 500 µL of radioimmunoassay (RIA) buffer containing 0.1% Triton X-100, 0.2% bovine serum albumin, and 0.02% $NaN_3$ in phosphate-buffered saline.

Diluted samples (200 µL) obtained from the above enzyme assay are incubated at 4° C. overnight with 25 µL each of [$^{125}$I]ET-1 (10,000 cpm/tube) and 1:20,000-fold diluted rabbit antibodies that recognize specifically the carboxyl terminal tryptophan of ET-1. Goat anti-rabbit antibodies coupled to magnetic beads (70 µg) are then added to each tube, and the reaction mixture is further incubated for 30 min at room temperature. The beads are pelleted using a magnetic rack. The supernatant is decanted, and the radioactivity in the pellet is counted in a gamma counter. Total and nonspecific binding are measured in the absence of nonradioactive ET-1 and anti-ET antibodies, respectively. Under these conditions, ET-1 and big ET-1 displace [$^{125}$I] ET-1 binding to the antibodies with $IC_{50}$ values of 21±2 and 260,000±66,000 fmol (mean±SEM, n=3–5), respectively.

In order to determine the $IC_{50}$ value of an inhibitor, a concentration-response curve of each inhibitor is determined. An IBM-compatible version of ALLFIT program is used to fit data to a one-site model.

In vitro testing is most appropriate for the compounds wherein Y is 5-tetrazolyl or carboxyl.

Illustrative of the invention, the compound of Example 5j demonstrates an $IC_{50}$ of about 11 nM in the in vitro assay for rh-ECE-1 inhibition.

Endothelin converting enzyme inhibition can also be determined in vivo by measuring the inhibition of big ET-1-induced pressor response in the anesthesized or conscious rat, as described below. The effect of the inhibitors on the pressor response resulting from big ET-1 challenge is measured in Sprague-Dawley rats as described in Biochem. Mol. Biol. Int. 31, (5), 861–867 (1993). Results are expressed as percent inhibition of the big ET-1-induced pressor response as compared to vehicle.

Male Sprague-Dawley rats are anesthetized with Inactin (100 mg/kg i.p.) and instrumented with catheters in the femoral artery and vein to record mean arterial pressure (MAP) and administer compounds, respectively. A tracheostomy is performed and a cannula inserted into the trachea to ensure airway patency. The body temperature of the animals is maintained at 37±1° C. by means of a heating blanket. Following surgery, MAP is allowed to stabilize before interrupting autonomic neurotransmission with chlorisondamine (3 mg/kg i.v.). Rats are then treated with the test compound at 10 mg/kg i.v. or vehicle and challenged with big ET-1 (1 nmol/kg i.v.) 15 min and 90 min later. Generally, the data are reported as the maximum increase in MAP produced by big ET-1 in animals treated with the test compound or vehicle.

Male Sprague-Dawley rats are anesthetized with methohexital sodium (75 mg/kg i.p.) and instrumented with catheters in the femoral artery and vein to measure mean arterial pressure (MAP) and administer drugs, respectively. The catheters are threaded through a swivel system that enables the rats to move freely after regaining consciousness. The rats are allowed to recover from this procedure for 24 h before initiating the study. On the following day, MAP is recorded via the femoral artery catheter and a test compound or vehicle is adminstered via the femoral vein. Animals are challenged with big ET-1 at 1 nmol/kg i.v. at various times after dosing. After an adequate washout period, depending upon the dose and regimen, animals can be re-tested at another dose of test compound or vehicle. Generally, the data are reported as the change in MAP produced by big ET-1 at 2-minute intervals in animals treated with the test compound as compared to vehicle.

ECE inhibition can also be determined in vivo by measuring the inhibition of the big ET-1 induced pressor response in conscious spontaneously hypertensive rats (SHR), e.g. as described in Biochem. Biophys. Res. Commun. 204, 407–412 (1994).

Male SHR (16–18 weeks of age) are administered either test compound or vehicle (1 M $NaHCO_3$) via an osmotic minipump implanted subcutaneously. On day 5 femoral arterial and venous catheters are placed in anesthetized rats for the measurement of MAP and for test compound administration, respectively. After a 48 hour recovery period, MAP is recorded (day 7) through the arterial catheter connected to a pressure transducer. Blood pressure and heart rate are allowed to stabilize for 30 min before ganglion blockade is performed using chlorisondamine (10/kg i.v.). Approximately 15 min later, a bolus dose of big ET-1 (0.25 nmol/kg i.v.) is administered to both vehicle- and test compound treated rats. The change in blood pressure in response to big ET-1 is then compared between the two groups of rats at 1, 5, 10, 15, 30 and 60 min after dosing using a two-way ANOVA.

The compounds of the invention inhibit cerebrovascular constriction and are useful for the treatment and alleviation of cerebral spasm. They are thus in turn useful for the treatment and alleviation of conditions in which cerebral vasospasm occurs. Such conditions include stroke, cerebral ischemia, acute and traumatic brain injury, brain hemorrhage, in particular aneurysmal subarachnoid hemorrhage, as well as migraine.

The inhibition of cerbral vasospasm is demonstrated by measuring the inhibition of experimentally induced constriction of basilar cerebral arteries in the rabbit (Caner et al., J. Neurosurg., 1996, 85, 917–922).

Bronchial effects can be determined by measuring the effect in a model of ET-1 induced bronchoconstriction.

Compounds of the invention may also possess angiotensin converting enzyme (ACE) and neutral endopeptidase (NEP) inhibitory activity. Tests for determination thereof are described e.g. in U.S. Pat. No. 5,506,244 which is incorporated herein by reference.

The combined effect is beneficial for e.g. the treatment of cardiovascular disorders in mammals such as hypertension, congestive heart failure and renal failure.

The compounds of the invention can generally be prepared according to methodology described in U.S. Pat. No. 5,506,244, in particular using the processes described and illustrated below, e.g.

(a) by condensing a compound of formula IV

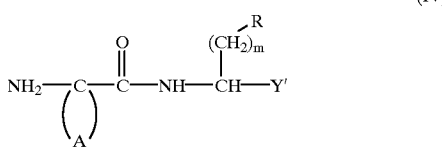
(IV)

wherein the symbols R, m and A have the meaning as defined above and Y' represents N-protected 5-tetrazolyl or esterified carboxyl, with a carboxylic acid of the formula V

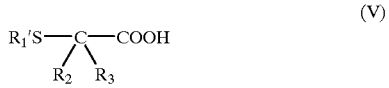
(V)

or a reactive funcitonal derivative thereof, wherein $R_2$ and $R_3$ have meaning as defined above, $R_1'$ represents a labile S-protecting group, e.g. acyl, t-butyl or optionally substituted benzyl; or (b) by condensing a compound of the formula VI

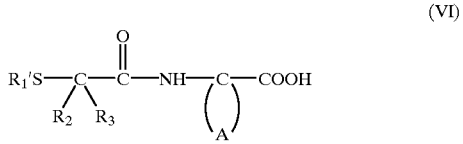
(VI)

or a reactive functional derivative thereof wherein the symbols A, $R_1'$, $R_2$ and $R_3$ have meaning as defined above, with a compound of the formula VII

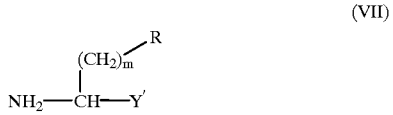
(VII)

wherein R, m, X and Y' have meaning as defined above; or (c) by condensing under basic conditions a compound of the formula

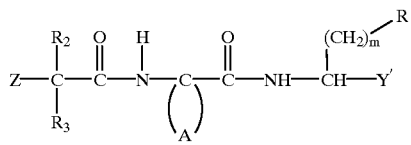
(VIII)

wherein the symbols R, A, $R_2$, $R_3$, and Y' have meaning as defined above and Z represents a reactive esterified hydroxyl group (e.g. halo such as chloro or bromo) as a leaving group, with a compound of the formula

$R_1'SH$ (IX)

wherein $R_1'$ represents a labile S-protecting group, e.g. acyl, t-butyl or optionally substituted benzyl;
and converting a resulting product wherein $R_1'$ is optionally substituted benzyl to a compound of formula I wherein $R_1$ is hydrogen; and in above said process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are converted to the compounds of the invention in manner described herein, functional groups present, such as thiol, carboxyl, amino and hydroxyl groups, are optionally protected by conventional protecting groups that are common in preparative organic chemistry. Protected thiol, carboxyl, amino and hydroxyl groups are those that can be converted under mild conditions into free thiol, carboxyl, amino and hydroxyl groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P. G. M. Woots, "Protective Groups in Organic Synthesis", Wiley, N.Y. 1991, "The Peptides", Vol. I, Schroeder and Luebke, Academic Press, London, N.Y., 1965, and also in P. J. Kocienski, "Protecting Groups", Thieme, N.Y. 1994.

Suitable protecting groups for the preparation of the 5-tetrazolyl compounds are the protecting groups customarily used in tetrazole chemistry, especially triphenylmethyl, unsubstituted or substituted, (for example nitro-substituted), benzyl such as 4-nitrobenzyl, lower alkoxymethyl such as methoxy- and ethoxymethyl, also 1-ethoxyethyl, lower alkylthiomethyl such as methylthiomethyl, silyl such as tri-lower alkylsilyl, for example dimethyl-tert-butyl- and triisopropyl-silyl, and also 2-cyanoethyl, also lower alkoxy-lower alkoxy-methyl, such as 2-methoxyethoxymethyl, benzyloxymethyl and phenacyl.

The removal of the protecting groups is carried out in accordance with known methods. For example, the triphenylmethyl group is customarily removed by hydrolysis, especially in the presence of an acid, or by hydrogenolysis in the presence of a hydrogenation catalyst; 4-nitrobenzyl is removed, for example, by hydrogenolysis in the presence of a hydrogenation catalyst; methoxy- or ethoxy-methyl is removed, for example, by treatment with a tri-lower alkyl-, such as triethyl- or tributyl-tin bromide; methylthiomethyl is removed, for example, by treatment with trifluoroacetic acid; silyl radicals are removed, for example, by treatment with fluorides, such as tetra-lower alkyl-ammonium fluorides, for example tetrabutylammonium fluoride, or alkali metal fluorides, for example sodium fluoride; 2-cyanoethyl is removed, for example, by hydrolysis, for example with sodium hydroxide solution; 2-methoxyethoxymethyl is removed, for example, by hydrolysis, for example with hydrochloric acid; and benzyloxymethyl and phenacyl are removed, for example, by hydrogenolysis in the presence of a hydrogenation catalyst.

A tetrazole protecting group, which is preferably introduced by conversion of a similarly protected amide to the corresponding N-substituted tetrazole, is e.g. cyanoethyl, p-nitrophenylethyl, lower alkoxycarbonylethyl, phenylsulfonylethyl and the like. Such tetrazole protecting groups can be removed by a retro-Michael deblocking reaction with a base such as DBN (1,5-diazabicyclo[4.3.0]non-5-ene), an amidine, an alkali metal carbonate or alkoxide, e.g. potassium carbonate, potassium t-butoxide, sodium methoxide in an inert solvent.

An amino protecting group is preferably t-butoxycarbonyl or benzyloxycarbonyl.

A sulfhydryl protecting group is preferably lower alkanoyl, e.g. acetyl.

The preparation of compounds of the invention according to process (a) involving the condensation of an amine of formula IV with the acid of formula V or a functional reactive derivative thereof, is carried out by methodology well-known for peptide synthesis.

The condensation according to process (a) of a compound of formula IV with a free carboxylic acid of formula V is carried out advantageously in the presence of a condensing agent such as dicyclohexylcarbodiimide or N-(3-dimethylaminopropyl)-N'-ethylcarbodiimide, and hydroxybenzotriazole, 1-hydroxy-7-azabenzotriazole, chlorodimethoxytriazine or benzotriazol-1-yloxy-tris-(dimethylamino)-phosphonium hexafluorophosphate (BOP Reagent), and triethylamine or N-methylmorpholine, in an inert polar solvent such as dimethylformamide or methylene chloride, preferably at room temperature.

The condensation of a compound of formula IV with a reactive functional derivative of an acid of formula V in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine, N-methylmorpholine or pyridine, preferably at room temperature.

Reactive functional derivatives of carboxylic acids of formula V are preferably acid halides (e.g. the acid chloride) and mixed anhydrides, such as the pivaloyl or isobutyloxycarbonyl anhydride, or activated esters such as benzotriazole, 7-azabenzotriazole or hexafluorophenyl ester.

The starting materials of formula IV can be prepared according to methods described herein and illustrated in the examples.

The preparation of a starting material of formula IV involves the acylation of an ester of the amino acid of formula X

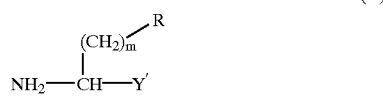

(X)

wherein R and Y' have meaning as defined hereinabove with an appropriately N-protected cyclic amino acid (or a reactive functional derivative) of formula XI

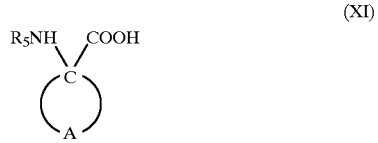

(XI)

wherein A has meaning as defined hereinabove and $R_5$ is a labile amino protecting group, e.g. t-butoxycarbonyl, to obtain the corresponding N-protected compound of formula IV.

The condensation of a compound of formula X with a compound of formula XI is carried out by methodology well known in peptide synthesis, e.g. as described above for the condensation of a compound of formula IV with a compound of formula V. The N-protecting group is removed according to methods well-known in the art, e.g. the t-butoxycarbonyl is removed with anhydrous acid such as trifluoroacetic acid.

The starting amino acids-and esters of compounds of formula X and XI are either known in the art or if new can be prepared according to methods well-known in the art, e.g. from the corresponding aldehyde or ketone. The α-amino acids of formula X are preferably obtained as the —S-enantiomers. Resolution of N-acyl amino acid esters can be performed by hydrolysis with an esterase, e.g. alcalase, to give the S-amino acid.

The starting materials of formula V are known or if new may be prepared according to conventional methods. The starting materials are prepared e.g. from the corresponding racemic or optically active α-amino acids, by conversion thereof to the α-bromo derivative followed by displacement thereof with the appropriate thio acids or optionally substituted benzylthiol, under basic conditions, for example as illustrated in European Patent application No. 524,553 published Jan. 27, 1993. S-Debenzylation of the resulting final products is carried out by reductive cleavage, e.g. with sodium in ammonia. S-Deacylation is carried out by e.g. base catalyzed hydrolysis with dilute aqueous sodium hydroxide or lithium hydroxide.

The preparation of the compounds of the invention according to process (b) involving the condensation of an acid of formula VI with a compound of formula VII is carried out in a similar fashion to process (a). Similarly the starting materials of formula VI are prepared by condensation of an acid of formula V with an ester corresponding to cyclic amino acids of formula XI ($R_5$ being hydrogen) under conditions similar to those described above, followed by removal of the carboxyl or tetrazolyl protecting group.

The preparation of the compounds of the invention according to process (c) involving the displacement of a leaving group Z in a compound of formula VIII with a sulfhydryl derivative $R_1'$—SH is carried out according to methods well-known in the art.

A reactive esterified hydroxyl group, represented by Z, is a hydroxyl group esterified by a strong inorganic or organic acid. Corresponding Z groups are in particular halo, for example chloro, bromo or iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The displacement is carried out in an inert solvent, such as dimethylformamide, methylene chloride or THF in the presence of a base such as potassium carbonate, triethylamine, diisopropylethylamine, N-methylmorpholine, and the like at room or elevated temperatures.

Similarly, the starting materials of formula VIII can be prepared by reacting the amide derivative of formula IV with an acid of the formula

(XII)

wherein $R_2$ and $R_3$ and Z have meaning as defined above, under conditions described for process (a).

Acids of formula XII, e.g. wherein Z is bromo, can be prepared from the corresponding α-aminoacids according to methods well known in the art. Optionally active acids of formula XII can be obtained from optically active α-aminoacids as illustrated herein.

The following sequences of reactions are illustrative of process (c).

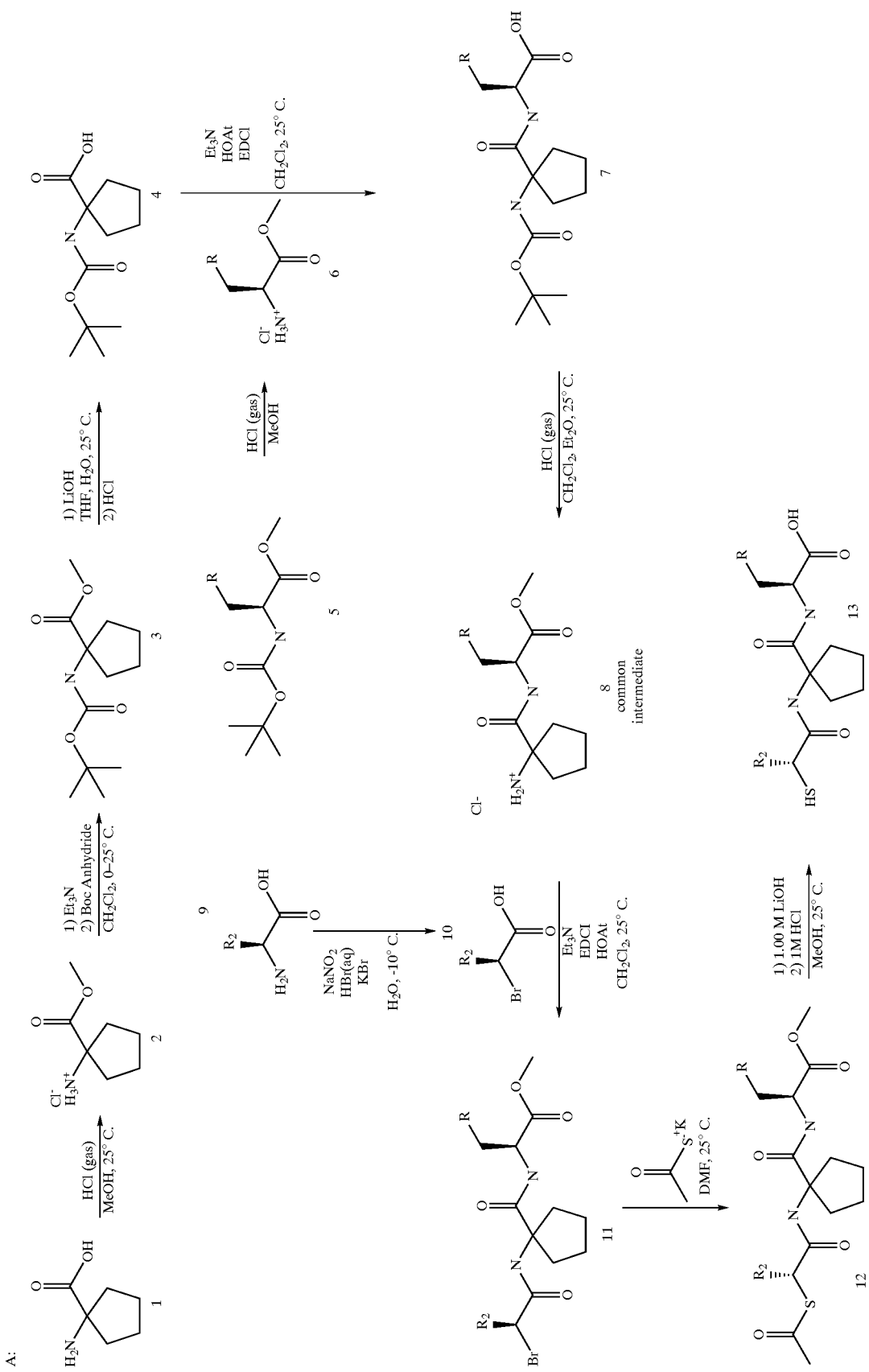

B: Alternatively for compounds wherein R is biaryl, e.g. N-Boc-cycloleucyl-biarylalanine derivatives 7 are prepared from the Suzuki coupling reactions of e.g. 2-[(1-tert-butoxy-carbonylamino-cyclopentanecarbonyl)-amino]-3-(4-trifuoromethanesulfonyloxyphenyl)-propionic acid ethyl ester 14 and various arylboronic acids according to a modification of the method reported by Carlson and Shieh (*J. Org. Chem.* 1992, 57, 379) using $PdCl_2(dppf)$ as the catalyst, $K_3PO_4$ as base, and DME or THF as solvent. The synthesis of the final products is then completed as in Sequence A.

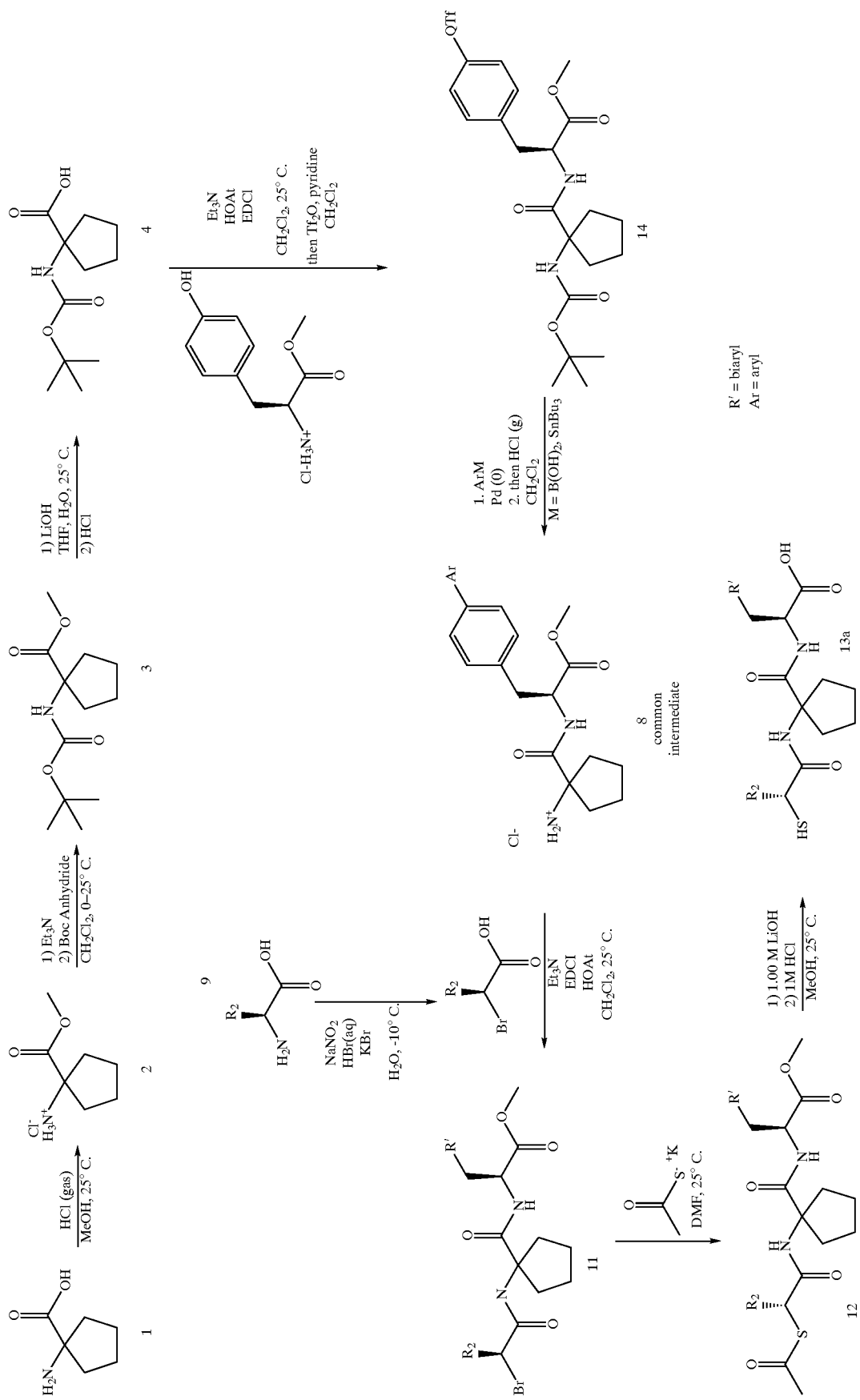

C: Alternatively, for compounds wherein R is biaryl the penultimate intermediate bromoesters 11 are synthesized from the standard coupling (DCC, HOAT, Et$_3$N in methylene chloride, as described above) of bromoacids 17 with amino ester hydrochlorides 5. The biarylamino ester hydrochlorides are in turn prepared e.g. from 2-(benzhydrylidene-amino)-3-[4-(4,4,5,5-tetramethyl-[1,3,2]dioxaborolan-2-yl-phenyl]-propionic acid ethyl ester 18 via Suzuki coupling and subsequent hydrolysis (Satoh, Y.; Gude, C.; Chan, K.; Firooznia, F. *Tetrahedron Lett.* 1997, 38, 7645).

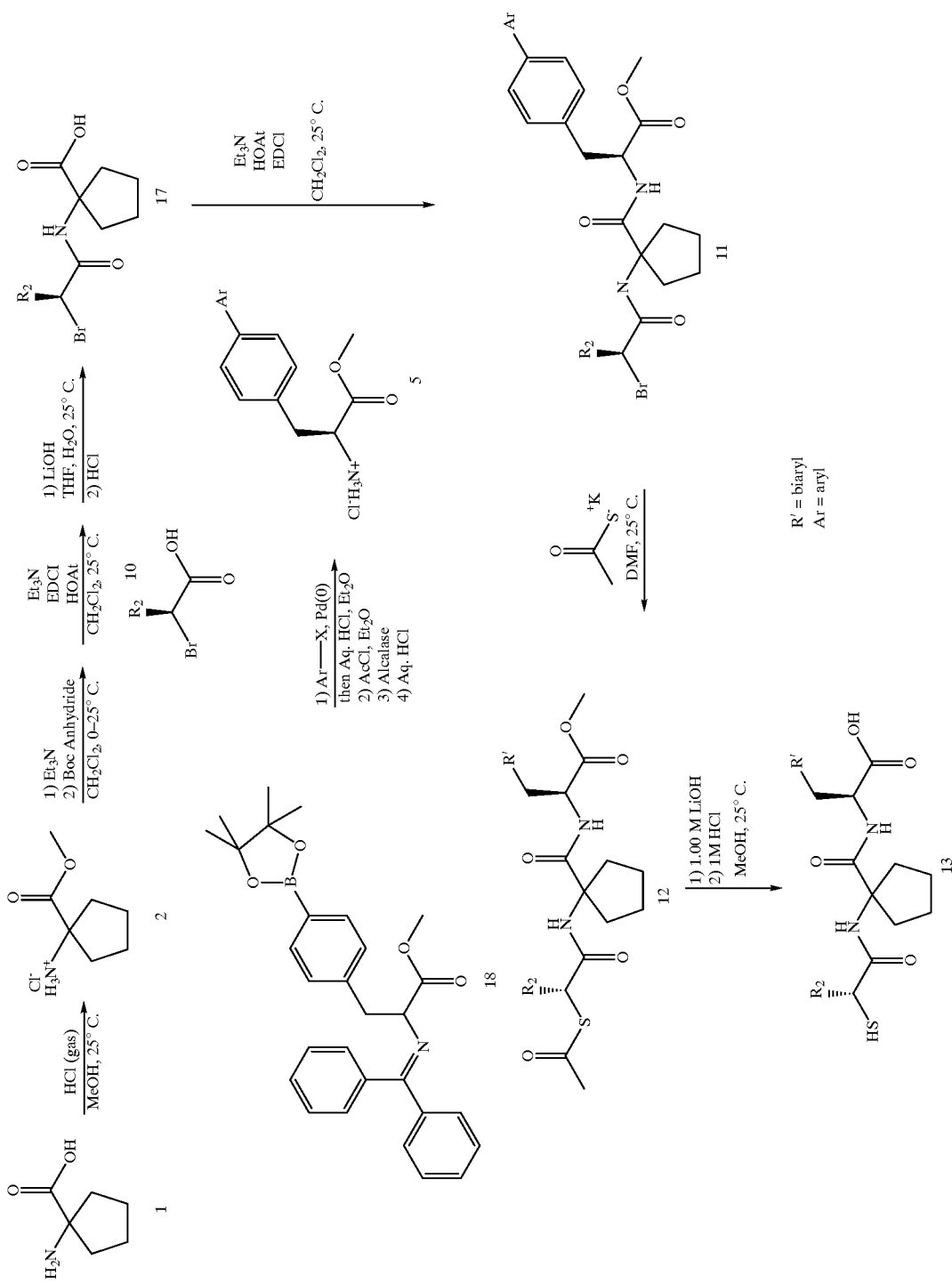

D: For compounds wherein R is biaryl, an alternative procedure for the preparation of the N-Boc-cycloleucyl-biarylalanine ester intermediates 7 involves the coupling of e.g. 2-[(1-tert-butoxycarbonylamino-cyclopentanecarbonyl)-amino]-3-(4-iodophenyl)-propionic acid methyl ester with various arylboronic acids according to the same reaction conditions as in Sequence B. The biaryl substituted intermediates 7 may also be obtained by coupling the iodophenyl substituted intermediate 19 with various arylstannates under the conditions of a palladium catalyzed Stille coupling reaction using toluene or dioxane as solvent.

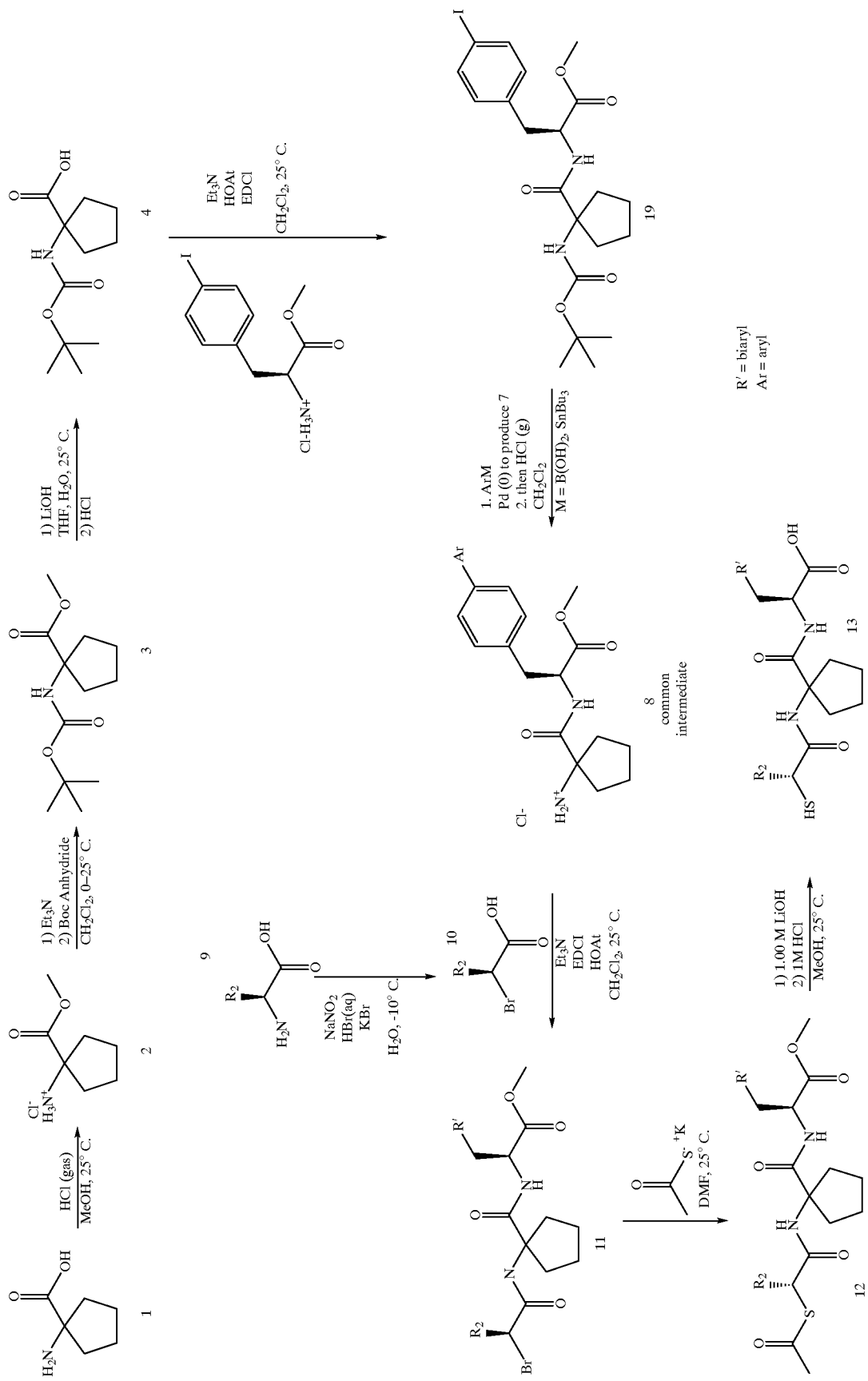

The compounds of the invention wherein Y represents 1H-5-tetrazolyl are similarly prepared, but starting with a tetrazole derivative of formula X'

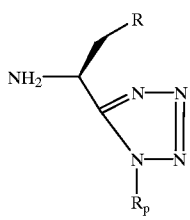

wherein $R_p$ is a tetrazolyl protecting group (such as 2-cyanoethyl).

The tetrazole starting materials of formula X' are prepared from the corresponding N-acyl amino acids by first converting such to the N—$R_p$-substituted amides. The resulting amides are then treated under conditions known in the art for tetrazole ring formation, e.g. under conditions described in Tetrahedron Letters 1979, 491 and J. Org. Chem. 56, 2395 (1991), e.g. with trimethylsilyl azide in the presence of diisopropyl azodicarboxylate and triphenylphosphine. Removal of the N-acyl group leads to the starting materials of formula X'.

In the above illustrated sequence of reactions for process (c) the tetrazole protecting group is preferably removed after formation of the bromo intermediate and prior to reaction with e.g. potassium thioacetate.

Certain compounds of the invention and intermediates can be converted to each other according to general reactions well known in the art.

The free mercaptans may be converted to the S-acyl derivatives by reaction with a reactive derivative of a carboxylic acid (corresponding to $R_1$ being acyl in formula I), such as an acid anhydride or said chloride, preferably in the presence of cobalt chloride ($CoCl_2$) in an inert solvent such as acetonitrile or methylene chloride.

The free mercaptans, wherein $R_1$ represents hydrogen, may be oxidized to the corresponding disulfides, e.g. by air oxidation or with the use of mild oxidizing agents such as iodine in alcoholic solution. Conversely, disulfides may be reduced to the corresponding mercaptans, e.g. with reducing agents such as sodium borohydride, zinc and acetic acid or tributylphosphine.

Carboxylic acid esters may be prepared from a carboxylic acid by condensation with e.g. the halide corresponding to the esterifying alcohol in the presence of a base, or with an excess of the alcohol, in the presence of an acid catalyst, according to methods well-known in the art.

Carboxylic acid esters and S-acyl derivatives may be hydrolyzed, e.g. with aqueous alkali such as alkali metal carbonates or hydroxides.

Carbocyclic or heterocyclic aromatic compounds or intermediates may be reduced to the corresponding alicyclic compounds or interemediates according to methods illustrated herein, e.g. by catalytic hydrogenation.

In case mixtures of stereoisomers (e.g. diastereomers) are obtained, these can be separated by known procedures such as fractional crystallization and chromatography (e.g. thin layer, column, flash chromatography). Racemic free acids can be resolved into the optical antipodes by fractional crystallization of d- or l- (α-methylbenzylamine, cinchonidine, cinchonine, quinine, quinidine, dehydroabietylamine, brucine or strychnine) salts and the like. Racemic products, if not diastereoisomers, can first be converted to diastereoisomers with optically active reagents (such as optically active alcohols to form esters) which can then be separated as described above, and e.g. hydrolyzed to the individual enantiomer. Racemic products can also be resolved by chiral chromatography, e.g. high pressure liquid chromatography using a chiral adsorbent; also by enzymatic resolution, e.g. of esters with alcalase.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, for inhibiting endothelin converting enzyme, and e.g. for the treatment of endothelin dependent disorders such as those mentioned hereinabove, e.g. cardiovascular disorders such as hypertension, heart-failure, acute and chronic renal failure, stroke and cerebral vasospasm, as well as bronchial asthma, erectile dysfunction, and complications associated with organ transplantation.

The present invention also relates to the use of the compounds of the invention for the preparation of pharmaceutical compositions, especially pharmaceutical compositions having endothelin converting enzyme inhibiting activity.

The pharmaceutical compositions according to the invention are those suitable for enteral, such as oral or rectal, transdermal and parenteral administration to mammals, including man, for the treatment of endothelin dependent disorders, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 5 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereof. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) or other wavelengths as specified in the examples.

The prefixes R and S are used to indicate the absolute configuration at each asymmetric center. L-Amino acids as used herein correspond to the S-configuration. The stereo chemical configuration, as assigned to the products of the examples, is indicated in a conventional manner in the respective structural formulae.

Abbreviations used are those standard in the art, e.g. "BOP" reagent is the abbreviation for benzotriazol-1-yloxy-tris(dimethylamino)phosphonium hexafluorophosphate, HOAT is the abbreviation for 1-hydroxy-7-azabenzotriazole, HOBT is the abbreviation for 1-hydroxybenzotriazole, EDCI is the abbreviation for 1-ehtyl-3-(3-dimethylaminopropyl) carbodiimide, hydrochloride, DCC is the abbreviation for dicyclohexylcarbodiimide.

EXAMPLE 1

Preparation of α-bromocarboxylic Acids (a) 5.00 g (38.1 mmol) of L-Norleucine (αS-aminohexanoic acid) and 22.7 g (191 mmol) of potassium bromide are dissolved in 50 mL of water at room temperature. Then 10.8 mL (95.5 mmol) of aqueous 48% hydrobromic acid is added and the mixture is cooled to −12° C. in an ice/NaCl bath. Next, the flask is equipped with an addition funnel containing 3.16 g (45.7 mmol) of sodium nitrite dissolved in 20 mL of water. The sodium nitrite solution is allowed to drip into the reaction mixture over the course of 30 minutes. After the addition of sodium nitrite is complete, the mixture is stirred for an additional 45 minutes, transferred to a separatory funnel, and diluted with ethyl acetate. The layers are separated and the aqueous phase is extracted two times with ethyl acetate. Combined ethyl acetate phases are washed three times with saturated aqueous sodium bisulfite (removing the yellow color), dried over sodium sulfate, and evaporated to dryness to afford a clear colorless oil which is dried under high vacuum to give αS-bromohexanoic acid. $^1$H NMR (250 MHz, CDCl$_3$) δ10.4 (s, 1 H), 4.24 (t, 1 H), 1.92–2.17 (m, 2 H), 1.32–1.55 (m, 4 H, 0.93 (t, 3 H).

Similarly prepared are:

(b) αR-bromohexanoic acid; $^1$H NMR (250 MHz, CDCl$_3$) δ9.80 (s, 1 H), 4.24 (t, 1 H), 1.81–2.26 (m, 2 H), 1.32–1.55 (m, 4 H), 0.93 (t, 3 H).

(c) αS-bromo-βR-methylpentanoic acid; $^1$H NMR (250 MHz, CDCl$_3$) δ10.88 (s, 1 H), 4.29 (d, 1 H), 1.86–2.09 (m, 0.5 H), 1.43–1.68 (m, 0.5 H), 1.24–1.43 (m, 2 H), 1.07 (d, 3 H), 0.95 (t, 3 H).

(d) αS-bromo-βS-methylpentanoic acid; $^1$H NMR (250 MHz, CDCl$_3$) δ10.35 (s, 1 H), 4.12 (d, 1 H), 1.98–2.10 (m, 0.5 H), 1.67–1.83 (m, 0.5 H), 1.24–1.48 (m, 2 H), 1.05 (d, 3 H), 0.92 (t, 3 H).

(e) αR-bromo-εR-methylpentanoic acid; $^1$H NMR (300 MHz, CDCl$_3$) δ10.65 (s, 1 H), 4.11 (d, 1 H), 1.99–2.10 (m, 0.5 H), 1.67–1.80 (m, 0.5 H), 1.22–1.44 (m, 2 H), 1.04 (d, 3 H), 0.91 (t, 3 H).

(f) αR-bromo-βS-methylpentanoic acid; $^1$H NMR (300 MHz, CDCl$_3$) δ10.15 (s, 1 H), 4.27 (d, 1 H), 1.90–2.06 (m, 0.5 H), 1.43–1.54 (m, 0.5 H), 1.22–1.38 (m, 2 H), 1.03 (d, 3 H), 0.93 (t, 3 H).

(g) αR-bromo-γ-methylpentanoic acid; $^1$H NMR (250 MHz, CDCl$_3$) δ9.81 (s, 1 H), 4.29 (d, 1 H), 1.92 (t, 2 H), 1.72–1.89 (m, 1 H), 0.97 (d, 3 H), 0.92 (d, 3 H).

(h) αS-bromo-γ-methylpentanoic acid; $^1$H NMR (250 MHz, CDCl$_3$) δ9.94 (s, 1 H), 4.35 (d, 1 H), 1.94 (t, 2 H), 1.69–1.93 (m, 1 H), 0.94 (d, 3 H), 0.89 (d, 3 H).

(i) αR-bromo-γ-thiomethylbutanoic acid; $^1$H NMR (250 MHz, CDCl$_3$) δ9.56 (s, 1 H), 4.50 (dd, 1 H), 2.57–2.76 (m, 2 H), 2.22–2.43 (m, 2H), 2.11 (s, 3 H).

(j) αS-bromo-γ-thiomethylbutanoic acid; $^1$H NMR (250 MHz, CDCl$_3$) δ10.18 (s, 1 H), 4.50 (dd, 1 H), 2.56–2.76 (m, 2 H), 2.20–2.43 (m, 2 H), 2.11 (s, 3 H).

(k) αR-bromopentanoic acid; $^1$H NMR (250 MHz, CDCl$_3$) δ10.06 (s, 1 H), 4.25 (dd, 1 H), 1.91–2.15 (m, 2 H), 1.34–1.62 (m, 2 H), 0.97 (t, 3 H).

(l) αS-bromopentanoic acid; $^1$H NMR (250 MHz, CDCl$_3$) δ10.70 (s, 1 H), 4.25 (dd, 1 H), 1.93–2.14 (m, 2 H), 1.34–1.62 (m, 2 H), 0.96 (t, 3 H).

(m) αR-bromo-βR-methoxybutanoic acid; $^1$H NMR (300 MHz, CDCl$_3$) δ8.62 (s, 1 H), 4.35 (d, 1 H), 4.77 (p, 1 H), 3.43 (s, 3 H), 1.32 (d, 3 H).

(n) αR-bromopropanoic acid; $^1$H NMR (250 MHz, CDCl$_3$) δ9.76 (s, 1 H), 4.40 (q, 1 H), 1.85 (d, 3 H).

(o) αR-bromo-βS-hydroxybutanoic acid; $^1$H NMR (300 MHz, CDCl$_3$) δ6.60 (broad s, 2 H), 4.28 (d, 1 H), 4.13–4.21 (m, 1 H), 1.33 (d, 3 H).

(p) αS-bromo-βR-hydroxybutanoic acid; $^1$H NMR (300 MHz, CDCl$_3$) δ6.66 (broad s, 2 H), 4.29 (d, 1 H), 4.10–4.21 (m, 1 H), 1.34 (d, 3 H).

(q) α-bromo-β-phenyl-propionic acid 10; $^1$H NMR (250 MHz, CDCl$_3$) δ7.25 (m, 5 H), 4.40 (t, 1 H), 3.45 (dd, 1 H), 3.25 (dd, 1 H); IR (CH$_2$Cl$_2$, cm$^{-1}$) 1755, 1722, 1603, 1495.

(r) α-bromo-β-naphthalen-2-yl-propionic acid; $^1$H NMR (250 MHz, CDCl$_3$) δ7.50–7.90 (m, 4 H), 7.25–7.50 (m, 3 H), 4.50 (t, 1 H), 3.55–3.65 (m, 1 H), 3.25–3.45 (m, 1 H); IR (CH$_2$Cl$_2$, cm$^{-1}$) 1752, 1720, 1599, 1510, 1147, 822. [a]$_D$+12.146 (10.55 mg/mL in CH$_2$Cl$_2$).

(s) β-biphenyl-4-yl-α-bromopropionic acid; $^1$H NMR (250 MHz, CDCl$_3$) δ7.20–7.60 (m, 9 H), 4.45 (t, 1 H), 3.50 (dd, 1 H), 3.25 (dd, 1 H).

(t) α-bromo-β-cyclohexyl-propionic acid; White solid; $^1$H NMR (250 MHz, CDCl$_3$) δ9.24 (s, 1 H), 4.01 (s, 1 H), 2.03–2.10 (m, 1 H), 1.50–1.95 (m, 5 H), 0.94–1.36 (m, 5 H); IR (KBr, cm$^{-1}$) 1753, 1716, 1112. [a]$_D$+36.104 (10.1 mg/mL in CH$_2$Cl$_2$).

EXAMPLE 2

(a) 2.54 g (4.67 mmol) of crude αS-bromohexanoylcycloleucyl-L-biphenylalanine methyl ester is dissolved in DMF at room temperature. To the solution is added 2.67 g (23.4 mmol) of potassium thioacetate. The reaction mixture is stirred for four hours and then is diluted with ether and washed successively four times with 250 mL of water and one time with 200 mL of brine. The etheral phase is then dried over sodium sulfate and concentrated to afford a brown residue. The crude product is purified by chromatography on silica gel with 30% ethyl acetate/hexane to provide αR-(acetylthio)-hexanoyl-cycloleucyl-L-biphenylalanine methyl ester as a white powder; $^1$H NMR (250 MHz, CDCl$_3$) δ7.18–7.60 (m, 9 H), 7.05 (d, 1 H), 6.40 (s, 1 H), 4.83 (dd, 1 H), 3.82 (s, 3 H), 1.45–2.24 (m, 10 H), 1.25–1.32 (m, 4 H).

The starting material is prepared as follows:

20.0 g (155 mmol) of cycloleucine (1-amino-1-cyclopentanecarboxylic acid), is taken up in 150 mL of absolute methanol at room temperature to give a cloudy white solution. Then hydrogen chloride gas is bubbled through the solution for 15 minutes, after which the flask is equipped with a bubbler and the mixture stirred for an additional 5 hours and 45 minutes at room temperature. The reaction mixture is concentrated to dryness and further dried under high vacuum for 30 minutes to afford a white solid. The white powder is triturated with ether and then filtered. After washing with more ether, the white solid is dried under high vacuum overnight to afford cycloleucine methyl ester hydrochloride.

27.0 g (151 mmol) of cycloleucine methyl ester hydrochloride is taken up in 250 mL of dichloromethane at room temperature to give a cloudy solution. The solution is cooled to 0° C. in an ice bath and then 44.3 mL (317 mmol) of triethylamine is added with rapid stirring for five minutes. Then 69.2 g (317 mmol) of di-tert-butyl dicarbonate is added neat and the mixture is allowed to warm to room temperature and stirred for 16 hours. The crude reaction mixture is concentrated to dryness to afford a white solid which is then dissolved in 200 mL of 90% THF in water. To this clear colorless solution is added 25.6 mL (317 mmol) of pyridine and the mixture is stirred for two hours at room temperature. The reaction mixture is concentrated to afford a light yellow residue which is taken up in ethyl acetate and washed sequentially two times with water, two times with 1M hydrochloric acid, two times with saturated sodium bicarbonate, and two times with brine. The organic phase is then dried over sodium sulfate and concentrated to afford N-t-Boc-cycloleucine methyl ester; $^1$H NMR (250 MHz, CDCl$_3$) δ4.85 (s, 1 H), 3.71 (s, 3 H), 2.14–2.15 (m, 2 H), 1.81–1.91 (m, 2 H), 1.73–1.80 (m, 4 H), 1.42 (s, 9 H).

25.5 g (105 mmol) of N-t-Boc cycloleucine methyl ester is dissolved in 900 mL of tetrahydrofuran at room temperature. Then 420 mL (420 mmol) of 1.0 M aqueous lithium hydroxide is added with rapid stirring. After stirring for 16 hours, the tetrahydrofuran is removed with the rotary evaporator after which the aqueous phase is washed two times with dichloromethane and then acidified to pH=1 using concentrated hydrochloric acid. The product is extracted into ethyl acetate. The organic phase is dried over sodium sulfate and then concentrated to dryness to afford a clear off-white oil which is dried under high vacuum to afford N-t-Boc-cycloleucine as a white amorphous foam; $^1$H NMR (250 MHz, DMSO) δ12.10 (s, 1 H), 7.09 (s, 1 H), 1.90–1.98 (m, 4 H), 1.60 (s, 4 H), 1.35 (s, 9 H).

50.0 g (146 mmol) of N-t-Boc-L-biphenylalanine is dissolved in 300 mL of absolute methanol at room temperature to give a clear and colorless solution. Then hydrogen chloride gas is bubbled through the solution for 15 minutes causing the solution to turn cloudy white. The flask is equipped with a bubbler and the solution stirred at room temperature for 3 hours. The reaction mixture is concentrated and then placed on the high vacuum for 30 minutes to afford a very light yellow powder which is triturated with 550 mL of ether and then filtered to afford a white solid which is washed with 300 mL more ether. The white powder is dried under high vacuum overnight to afford L-biphenylalanine methyl ester hydrochloride; $^1$H NMR (250 MHz, DMSO) δ8.67 (s, 3 H), 7.31–7.68 (m, 9 H), 4.32 (t, 1 H), 3.70 (s, 3 H), 3.24 (t, 2 H).

18.5 g (80.7 mmol) of N-t-Boc-cycloleucine is dissolved in 400 mL of dichloromethane at room temperature. With rapid stirring, are added sequentially: 25.9 g (88.7 mmol) of L-biphenylalanine methyl ester hydrochloride; 16.8 mL (121 mmol) of triethylamine, 12.1 g (88.7 mmol) of HOAt, and 30.9 g (161 mmol) of the water soluble coupling reagent EDCI. After stirring for 18 hours, the brown mixture is diluted with ether and washed three times with water, two times with 1M hydrochloric acid, two times with saturated sodium bicarbonate, and two times with brine. The organic phase is then dried over sodium sulfate and concentrated to dryness. The resulting white solid is then dried under high vacuum to yield N-t-Boc-cycloleucyl-L-biphenylalanine methyl ester; $^1$H NMR (300 MHz, CDCl$_3$) δ7.17–7.56 (m, 10 H), 4.87 (dd, 1 H), 4.74 (s, 1 H), 3.69 (s, 3 H), 3.14 (dd, 2 H), 2.14–2.25 (m, 2 H), 1.60–1.90 (m, 6 H), 1.38 (s, 9 H).

36.0 g (77.1 mmol) of N-t-Boc-cycloleucyl-L-biphenylalanine methyl ester is dissolved in 400 mL of 3:1 dichloromethane/ether at room temperature to give a semi clear solution. With rapid stirring, hydrogen chloride gas is bubbled through the solution for 15 minutes causing the solution to turn cloudy white. The flask is equipped with a bubbler and the solution stirred at room temperature for 3.5 hours. The reaction mixture is concentrated and then placed on the high vacuum for 30 minutes to afford a light yellow amorphous solid. The solid is dissolved in warm dichloromethane and crystallized by the addition of hexane. The off-white solid that is precipitated from solution is filtered, washed with cold hexane, and dried under high vacuum to afford cycloleucyl-L-biphenylalanine methyl ester hydrochloride; $^1$H NMR (250 MHz, DMSO) δ8.71 (d, 1 H), 8.18 (s, 3 H), 7.31–7.65 (m, 9 H), 4.55–4.65 (m, 1 H), 3.66 (s, 3 H), 3.00–3.23 (m, 2 H), 2.05–2.22 (m, 2 H), 1.62–2.00 (m, 6 H).

2.00 g (4.96 mmol) of Cycloleucyl-L-biphenylalanine methyl ester hydrochloride, 1.06 g (5.46 mmol) of 2S-bromohexanoic acid, and 743 mg (5.46 mmol) of HOAt are dissolved in 30 mL of dichloromethane at room temperature. To the solution is added 1.18 mL (8.43 mmol) of triethylamine, 1.91 g (9.92 mmol) of 1-(3-dimethylaminopropyl)-3-ethylcarbodiimide hydrochloride (EDCI) coupling reagent, and the reaction mixture is stirred for 15 hours. The reaction mixture is then diluted with ether and washed successively three times with water, two times with 1M hydrochloric acid, two times with saturated sodium bicarbonate, and two times with brine. The etheral phase is then dried over sodium sulfate and concentrated to afford αS-bromohexanoylcycloleucyl-L-biphenylalanine methyl ester, as a light yellow solid.

(b) Similarly prepared is αS-(acetylthio)-pentanoyl-cycloleucyl-L-biphenylalanine methyl ester, mp 130–134° C.

EXAMPLE 3

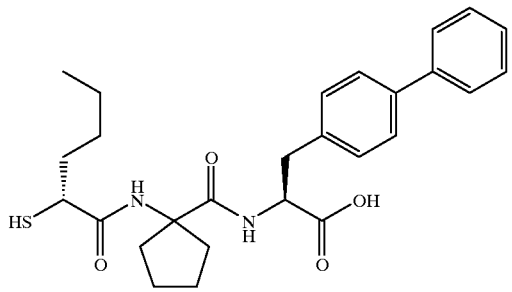

189 mg (0.351 mmol) of 2R-(acetylthio) hexanoylcycloleucyl-L-biphenyl-alanine methyl ester is dissolved in 4 mL of methanol at room temperature. Then 1.4 g (1.4 mmol) of aqueous 1.00 M lithium hydroxide is added. The clear colorless mixture is stirred for two hours and then acidified to pH=1 with 1M hydrochloric acid causing a white precipitate to form. The white solid is extracted into ethyl acetate, washed with brine, dried over sodium sulfate, and concentrated to dryness to afford an off-white solid which is further dried under high vacuum in a 50° C. oven to yield 3-biphenyl-4-yl-2-{[1-(2R-mercapto-hexanoylamino)-cyclopentanecarbonyl]-amino}-propionic acid; mp 104–107° C.

EXAMPLE 4

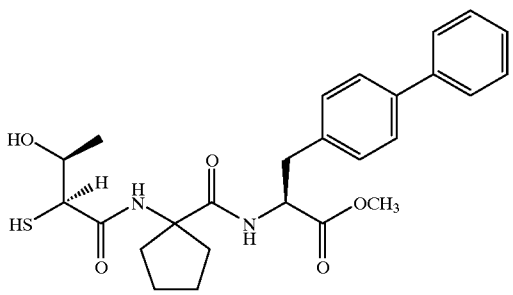

500 mg (0.94 mmol) of αR-bromo-βS-hydroxybutanoylcycloleucyl-L-biphenylalanine methyl ester is dissolved in 3 mL of methanol, and treated with 530 mg (9.4 mmol) of sodium hydrosulfide hydrate overnight at room temperature. The reaction mixture is evaporated to dryness to afford a yellow solid which is taken up in ethyl acetate, acidified to pH=1 with 1M hydrochloric acid, and the phases are separated. The organic phase is washed with brine, dried over sodium sulfate, and concentrated to dryness to give a yellow oil. Drying under high vacuum then affords αS-mercapto-βS-hydroxybutanoyl-cycloleucyl-L-biphenylalanine methyl ester; $^1$H NMR (300 MHz, CDCl$_3$) δ7.16–7.54 (m, 10 H), 6.24 (s, 1 H), 4.87 (dd, 1 H), 3.72–3.90 (m, 1 H), 3.71 (s, 3 H), 3.08–3.21 (m, 2 H), 3.00 (dd, 1 H), 2.36 (s, 1 H), 1.68–2.41 (m, 9 H), 1.25 (d, 3 H).

The starting material is prepared from αR-bromo-βS-hydroxybutanoic acid.

EXAMPLE 5

Similarily prepared according to procedures described in the previous examples are the following compounds of the formula

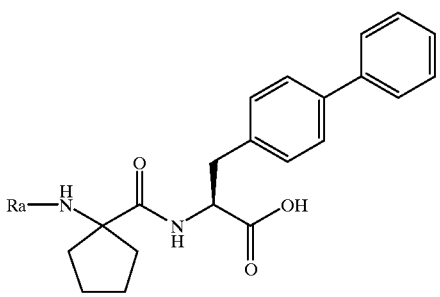

in which
(a) Ra=αS-mercaptohexanoyl; mp 159–162° C.;
(b) Ra=αR-mercapto-βR-methylpentanoyl; mp 172–174° C.;
(c) Ra=αR-mercapto-βS-methylpentanoyl; mp 108–116° C.;
(d) Ra=αS-mercapto-βR-methylpentanoyl; mp 190–191° C.;
(e) Ra=αS-mercapto-βS-methylpentanoyl; mp 142–145° C.;
(f) Ra=αS-mercapto-γ-methylpentanoyl; mp 187–189° C.;
(g) Ra=αR-mercapto-γ-methylpentanoyl; mp 120–124° C.;
(h) Ra=αS-mercapto-γ-methylthiobutanoyl; 159–163° C.;
(i) Ra=αR-mercapto-γ-methylthiobutanoyl; mp 159–163° C.;
(j) Ra=αS-mercaptopentanoyl; mp 180–182° C.;
(k) Ra=αR-mercaptopentanoyl; mp 77–85° C.;
(l) Ra=αR-mercapto-βR-methoxybutanoyl; mp 130–132° C.;
(m) Ra=αS-mercaptopropanoyl; mp 185–187° C.;
(n) Ra=αS-mercapto-βS-hydroxybutanoyl; mp 120–124° C.;
(o) Ra=αR-mercapto-βR-hydroxybutanoyl; mp 155–160° C.;
(p) Ra=αS-mercapto-β-methylbutanoyl; mp 180–181° C.

EXAMPLE 6

Similarly prepared according to procedures described in the previous examples are the following:

(a)

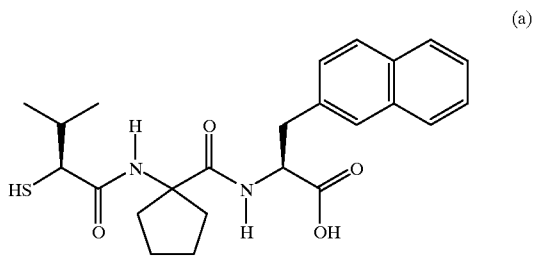

2-{[1-(2-Mercapto-3-methyl-butanoylamino)-cyclopentanecarbonyl]-amino}-3-naphthalen-2-yl-propionic acid; mp 197–195° C.

(b)

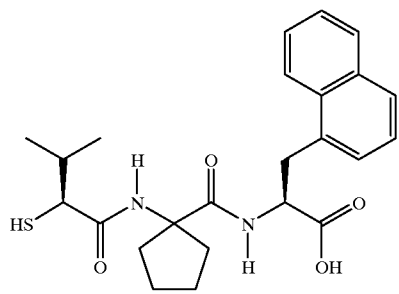

2-{[1-(2-Mercapto-3-methyl-butanoylamino)-cyclopentanecarbonyl]-amino}-3-naphthalen-1-yl-propionic acid; mp 207° C.

(c)

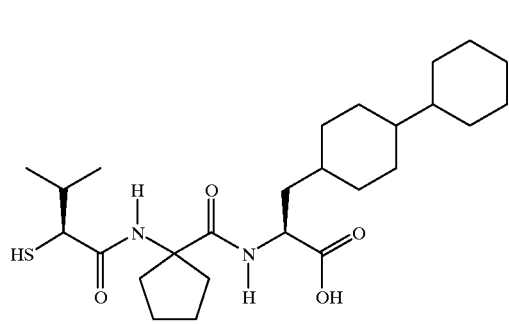

3-Bicyclohexyl-4-yl-2-{[1-(2-mercapto-3-methyl-butanoylamino)-cyclopentanecarbonyl]-amino}-propionic acid; mp 209–210° C.

The 3-bicyclohexyl-4-yl-2-tert-butoxycarbonylamino-propionic acid intermediate is prepared as follows:

A suspension of 3-biphenyl-4-yl-2-tert-butoxycarbonylaminopropionic acid (5.0 g) and platinum oxide (0.625 g) in 40 mL of EtOH is pressurised with $H_2$ at 45 psi, and stirred at room temperature for 2 hours. The catalyst is filtered and washed twice with EtOH. The EtOH solution is then concentrated in vacuo and the residue is recrystallized from hexane to obtain the intermediate; $^1$H NMR (300 MHz, CDCl$_3$) δ5.50–6.60 (br s, 1 H), 4.90 (d, 1 H), 4.05–4.30 (m, 1 H), 1.80–2.0 (m, 1 H), 1.55–1.80 (m, 6 H), 1.25–1.55 (m, 7 H), 1.47 (s, 9 H), 1.05–1.25 (m, 5 H), 0.75–1.05 (m, 3 H).

(d)

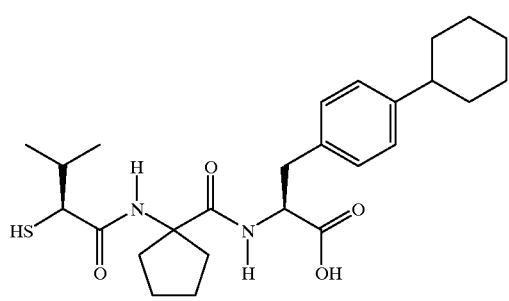

3-(4-Cyclohexyl-phenyl)-2-{[1-(2-mercapto-3-methylbutanoylamino)-cyclopentanecarbonyl]-amino}-propionic acid; mp 201–202° C.

The 3-(4-cyclohexyl-phenyl)-2-tert-butoxycarbonylamino-propionic acid intermediate is prepared as follows:

A suspension of 3-biphenyl-4-yl-2-tert-butoxycarbonylamino-propionic acid (1.0 g) and 5% Rh/C (0.25 g) in 10 mL of EtOH is pressurised with $H_2$ at 45 psi, and stirred at room temperature for 24 hours. The catalyst is filtered and washed twice with EtOH. The EtOH phases are then concentrated in vacuo and the residue is purified by chromatography on silica gel (hexane:EtOAc:AcOH 80:20:1) to furnish a white solid. $^1$H NMR (250 MHz, CDCl$_3$) δ8.25 (br s, 2 H), 7.04 (s, 4 H), 6.05 (br s, 0.25 H), 4.95 (d, 0.5 H), 4.55 (d, 0.5 H), 4.35 (br m, 0.25 H), 2.75–3.20 (m, 1.5 H), 2.35–2.60 (m, 1 H), 1.55–1.90 (m, 6 H), 1.45 (s, 9 H), 1.20–1.50 (m, 4 H).

(e)

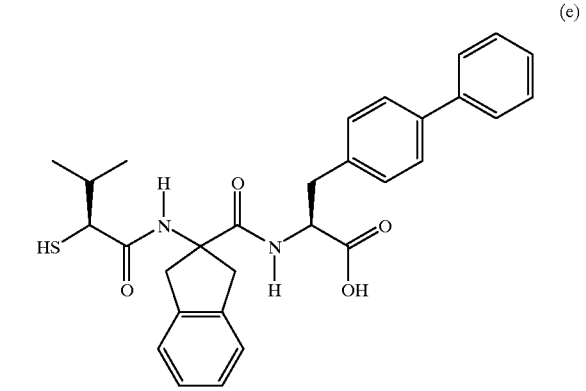

3-Biphenyl-4-yl-2-{[1-(2-mercapto-3-methylbutanoylamino)-indane-2-carbonyl]-amino}-propionic acid; mp 203–205° C.

(f)

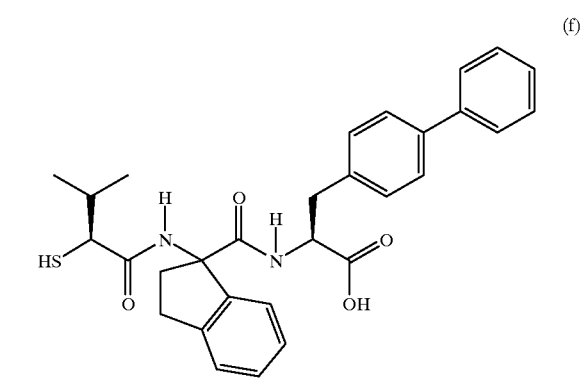

3-Biphenyl-4-yl-2-{[1-(2-mercapto-3-methyl-butyrylamino)-indane-1-carbonyl]-amino}-propionic acid; mp 115–120° C.

3.00 (d, 1 H), 2.70 (br s, 2 H), 2.10–2.40 (m, 2 H), 1.65–1.80 (m, 14 H), 1.37 (s, 9 H).

(g)

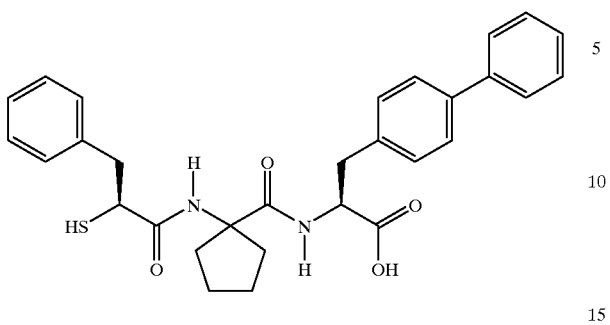

3-Biphenyl-4-yl-2-{[1-(2-mercapto-3-phenyl-propionylamino)-cyclopentanecarbonyl]-amino}-propionic acid; mp 212–213° C.

(h)

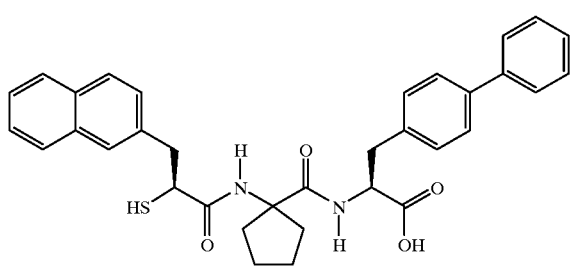

3-Biphenyl-4-yl-2-{[1-(2-mercapto-3-naphthalen-2-yl-propionylamino)-cyclopentanecarbonyl]-amino}-propionic acid; mp 166–168° C.

(i)

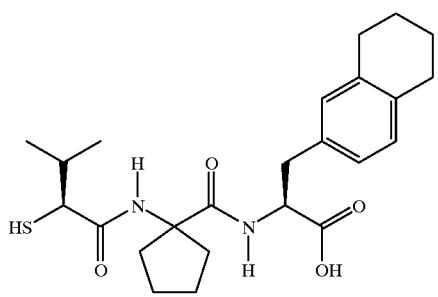

2-{[1-(2-Mercapto-3-methyl-butanoylamino)-cyclopentanecarbonyl]-amino}-3-(5,6,7,8-tetrahydro-naphthalen-2-yl)-propionic acid; mp 190–192° C.

The 2-[(1-tert-butoxycarbonylamino-cyclopentanecarbonyl)-amino]-3-(5,6,7,8-tetrahydro-naphthalen-2-yl)-propionic acid methyl ester intermediate is prepared as follows:

A suspension of 2-[(1-tert-butoxycarbonylamino-cyclopentanecarbonyl)-amino]-3-naphthalen-2-yl-propionic acid (400 mg, 0.908 mmol) and platinum oxide (400 mg) in 40 mL of MeOH is pressurized with $H_2$ at 42 psi for 39 hours. The catalyst is filtered off, and the filtrate is concentrated in vacuo. The residue is purified by chromatography on silica gel (33% EtOAc/hexane) to obtain the intermediate as a white solid. $^1$H NMR (250 MHz, $CDCl_3$) δ7.10 (s, 1 H), 6.90 (d, 1 H), 6.80 (d, 2 H), 4.80 (app q, 1 H), 3.75 (s, 3 H), (j)

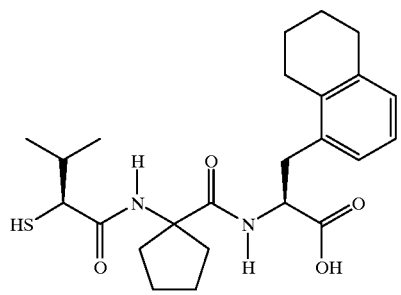

2-{[1-(2-Mercapto-3-methylbutanoylamino)-cyclopentanecarbonyl]-amino}-3-(5,6,7,8-tetrahydro-naphthalen-1-yl)-propionic acid; mp 158–164° C.

The 2-amino-3-(5,6,7,8-tetrahydro-naphthalen-1-yl)-propionic acid methyl ester hydrochloride intermediate is prepared as follows:

A suspension of 1-naphthylalanine methyl ester hydrochloride (500 mg, 1.79 mmol) and platinum oxide (170 mg) in 20 mL of MeOH is pressurized with $H_2$ at 42 psi for 3.5 hours. The catalyst is filtered off and the filtrate is concentrated in vacuo to furnish the intermediate as a solid; $^1$H NMR (250 MHz, $CDCl_3$) δ8.50–9.00 (br s, 1 H), 6.95–7.05 (m, 3 H), 4.20 (br s, 1 H), 4.20 (br d, 2 H), 3.45 (s, 3 H), 3.15–3.30 (br m, 1 H (½ of $CH_2$), the other ½ of $CH_2$ at 3.45,1 H), 2.65–2.75 (m, 4 H), 1.65–1.90 (m, 4 H).

(k)

2-{[1-(2-Mercapto-3-methylbutanoylamino)-cyclopentanecarbonyl]-amino}-3-(2-methoxybiphenyl-4-yl)-propionic acid; mp 121–123° C.

The 2-amino-3-(2-methoxybiphenyl-4-yl)-propionic acid methyl ester hydrochloride intermediate is prepared from 4-bromomethyl-2-methoxy-biphenyl according to the procedure reported by Williams and Im (*J. Am. Chem. Soc.* 1991, 113, 9726). White solid; $^1$H NMR (250 MHz, $CD_3OD$) δ7.25–7.47 (m, 6 H), 6.96 (s, 1 H), 6.92 (d, 1 H), 4.39 (dd, 1 H), 3.86 (s, 3 H), 3.81 (s, 3 H), 3.19 (dd, ½ of $CH_2$ ABX, 1 H, the other H buried under solvent peak).

The 4-bromomethyl-2-methoxy-biphenyl starting material is prepared as follows:

3-Methoxy-4-trifluoromethanesulfonyloxybenzaldehyde is prepared from 4-hydroxy-3-methoxybenzaldehyde oil; $^1$H NMR (250 MHz, $CD_3OD$) δ9.95 (s, 1 H), 7.55 (d, 1 H), 7.50 (dd, 1 H), 7.40 (d, 1 H), 3.97 (s, 3 H). Such is converted to 2-methoxy-biphenyl-4-carboxaldehyde according to the procedure reported in Chem. Rev. 1995, 95, 2457–83 for the coupling of tyrosine triflates and boronic acids, clear, colorless oil; ¹H NMR (250 MHz, CDCl₃) δ10.00 (s, 1 H), 7.30–7.60 (m, 8 H), 3.87 (s, 3 H).

10.0 mL of 1.0 M DIBAL-H (diisobutylaluminum hydride) in toluene is added to a solution of 2-methoxy-biphenyl-4-carboxaldehyde (1.34 g, 6.3 mmol) in 15 mL of THF. The cooling bath is removed and the reaction mixture is stirred for 30 minutes. 3 mL of MeOH is added to quench the reaction, and the resulting mixture is partitioned between EtOAc and 1N HCl. The organic phase is separated and washed with brine, dried over MgSO₄, filtered, and concentrated to yield 2-methoxy-biphenyl-4-yl)-methanol as a clear, colorless oil. ¹H NMR (250 MHz, CDCl₃) δ7.45–7.55 (m, 2 H), 7.20–7.45 (m, 4 H), 6.95–7.05 (m, 2 H), 4.75 (s, 2 H), 3.85 (s, 3 H); IR (CH₂Cl₂, cm⁻¹) 3602, 1612, 1279, 1164, 1041, 859, 826.

1.24g (7.6 mmol) of NBS (N-bromosuccinimide) is added in small portions to a solution of (2-methoxy-biphenyl-4-yl)-methanol (1.35 g, 6.3 mmol) and triphenyl phosphine (2.0 g, 7.0 mmol) in 15 mL of CH₂Cl₂ at 0° C. The cooling bath is removed and the reaction mixture is stirred at room temperature overnight. The reaction mixture is then concentrated in vacuo, and the residue is purified by chromatography on silica gel (10% EtOAc/hexane) to furnish 4-bromomethyl-2-methoxy-biphenyl as a clear, colorless oil. ¹H NMR (250 MHz, CDCl₃) δ7.45–7.55 (m, 2 H), 7.20–7.45 (m, 4 H), 7.05 (dd, 2 H), 7.0 (d, 1 H), 4.50 (s, 2 H), 3.80 (s, 3 H).

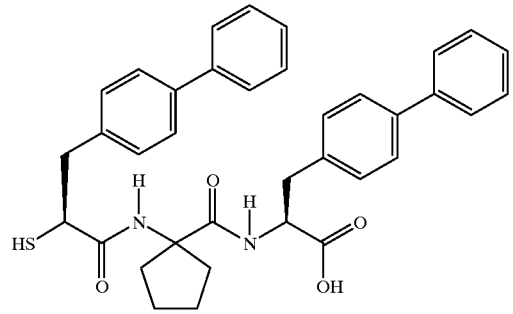

(l)

3-Biphenyl-4-yl-2-{1-[3-biphenyl-4-yl-2-mercapto-propionylamino)-cyclopentanecarbonyl]-amino}-propionic acid; mp 187–189° C.

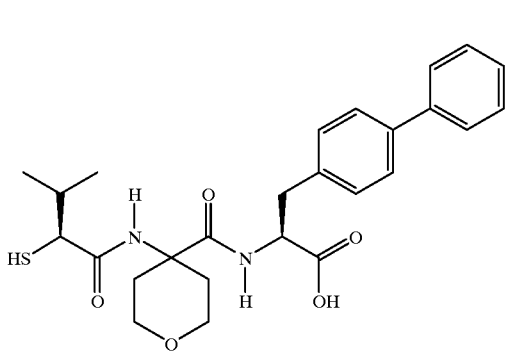

(m)

3-Biphenyl-4-yl-2-{[4-(2-mercapto-3-methyl-butanoylamino)-tetrahydro-pyran-4-carbonyl]-amino}-propionic acid; prepared from 4-amino-tetrahydropyran-4-carboxylic acid (Lewis et al, *J. Med. Chem.* 1978, 21, 1070); mp 161–163° C.

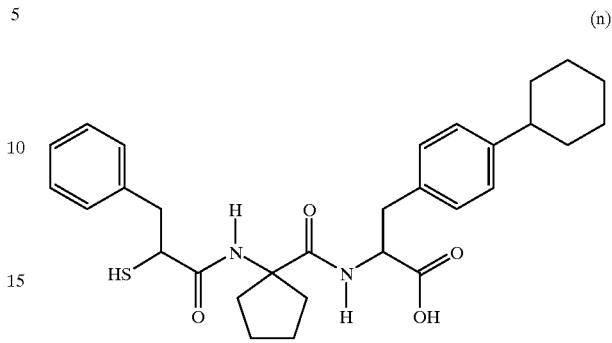

(n)

3-(4-Cyclohexyl-phenyl)-2-{[1-(2-mercapto-3-phenyl-propionylamino)-cyclopentanecarbonyl]-amino}-propionic acid; mp 172–175° C.

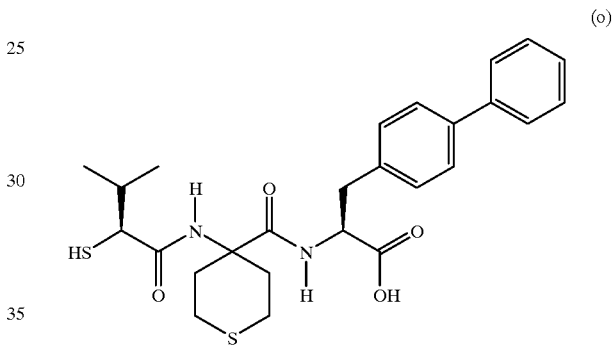

(o)

3-Biphenyl-4-yl-2-{[1-(2-mercapto-3-methyl-butanoylamino)-tetrahydro-thiopyran-4-carbonyl]-amino}-propionic acid; prepared from 4-amino-tetrahydro-thiopyran-4-carboxylic acid (*J. Med. Chem.* 1978, 21, 1070); mp 203–204° C.

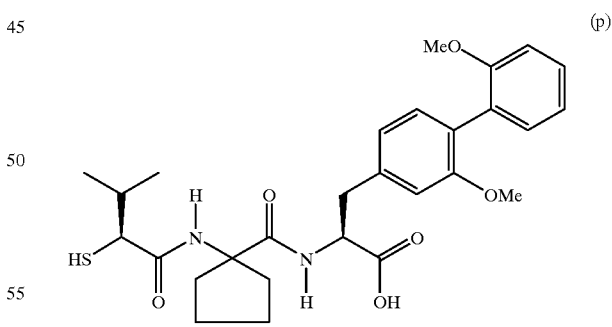

(p)

3-(2,2'-Dimethoxy-biphenyl-4-yl)-2-{[1-(2-mercapto-3-methyl-butanoylamino)-cyclopentanecarbonyl]-amino}-propionic acid; mp 173–175° C.

The starting material, 4-bromomethyl-2,2'-dimethoxy-biphenyl is prepared according to the procedure described above for the synthesis of 4-bromomethyl-2-methoxy-biphenyl; ¹H NMR (250 MHz, CDCl₃) δ7.35 (dt, 1 H), 7.20–7.28 (m, 2 H), 6.90–7.10 (m, 4 H), 4.53 (s, 2 H), 3.78 (s, 3 H), 3.76 (s, 3 H).

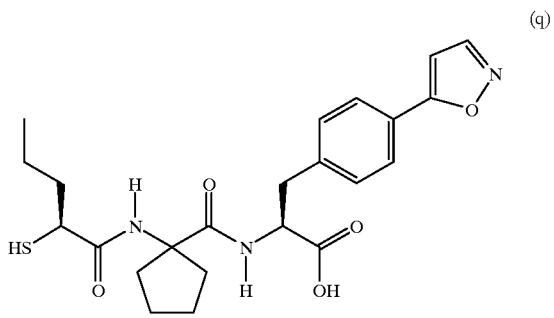

(q)

3-(4-Isoxazole-5-yl-phenyl)-2-{[1-(2-mercapto-pentanoylamino)-cyclopentanecarbonyl]-amino}-propionic acid; mp 95–108° C.

The starting material is prepared as follows:

Bisbenzoyl peroxide (560 mg, 0.232 mmol) is added to a solution of 2.17 g (13.65 mmol) of 5-(4-methyl-phenyl)-isoxazole (Lin, Y.-i.; Lang, Jr., S. A. *J. Org. Chem.* 1980, 45, 4857) and N-bromosuccinimide (2.43 g, 13.65 mmol) in 64 mL of $CCl_4$, and the reaction mixture is heated at reflux overnight. The reaction mixture is then concentrated in vacuo, and the product is purified by chromatography on silica gel (20% EtOAC/hexane, $R_f$=0.6) to yield 5-(4-bromomethyl-phenyl)-isoxazole. $^1H$ NMR (250 MHz., $CDCl_3$) δ8.30 (d, 1 H), 7.73 (d, 2 H), 7.45 (d, 2 H), 6.51 (d, 1 H), 4.50 (s, 2 H).

2-Amino-3-(4-isoxazole-5-yl-phenyl)-propionic acid hydrochloride is prepared according to the procedure of Stork et al. (*J. Org. Chem.* 1976, 41, 3491) using NaHMDS as the base, from 5-(4-bromomethyl-phenyl)-isoxazole; white solid; $^1H$ NMR (300 MHz, $CD_3OD$) δ8.43 (d, 1 H), 7.86 (d, 2H), 7.43 (d, 2 H), 6.81 (d, 1 H), 4.35 (t, 1 H), 4.25 (q, 2 H), 3.21–3.34 (m, 2 H), 1.23 (t, 3 H).

Conversion to 2-acetylamino-3-(4-isoxazol-5-yl-phenyl)-propionic acid ethyl ester followed by enzymatic hydrolysis using alcalase yields (S)-2-acetylamino-3-(4-isoxazole-5-yl-phenyl)-propionic acid $^1H$ NMR (300 MHz, $CD_3OD$) δ8.37 (d, 1 H), 7.75 (d, 2 H), 7.36 (d, 2 H), 7.70 (d, 1 H), 4.71 (dd, 1 H), 3.26 (dd, 1 H), 3.00 (dd, 1 H), 1.91 (s, 3 H). IR (KBr, $cm^{-1}$) 1734, 1621, 1549, 1512, 1466, 1192, 1127, 921, 778. $[\alpha]_D$+55.509 (9.969 mg/mL MeOH).

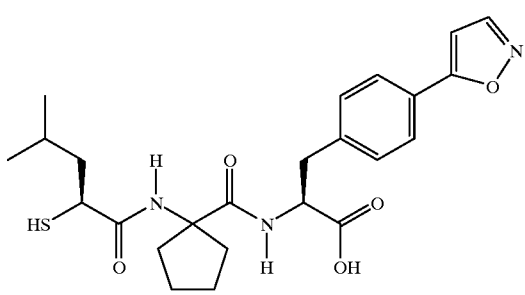

(r)

3-(4-Isoxazole-5-yl-phenyl)-2-{[1-(2-mercapto4-methyl-pentanoylamino)-cyclopentanecarbonyl]-amino}-propionic acid; mp 104–110° C.

EXAMPLE 7

Similarly prepared according to procedures previously described are:

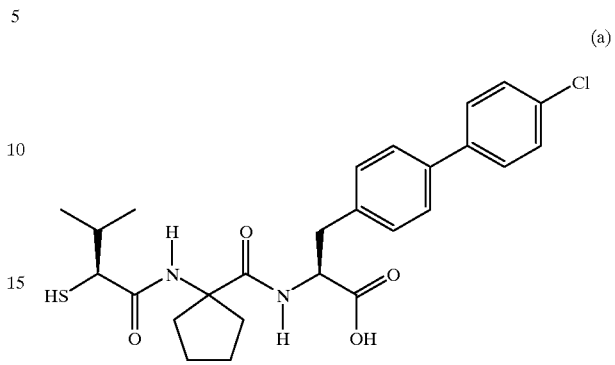

(a)

2-{[1-(2-Mercapto-3-methyl-butanoylamino)-cyclopentanecarbonyl]-amino}-3-(4'-chlorobiphenyl-4-yl)-propionic acid; mp 177–179° C.

The starting material is prepared as follows:

3.0 g (12.2 mmol) of tyrosine ethyl ester hydrochloride and 2.8 g (12.2 mmol) of N-Boc-cycloleucine are suspended in 10 mL of $CH_2Cl_2$. 1.65 g (12.2 mmol) of HOBT, 3.02 g (14.6 mmol) of DCC, and 1.7 mL (12.2 mmol) of $Et_3N$ are added, and the solution is stirred at room temperature overnight. The reaction mixture is filtered, and $CH_2Cl_2$ is removed in vacuo. The residue is taken up in EtOAc, filtered, and washed successively with 1N HCl, water, saturated aqueous $NaHCO_3$ solution, and brine, then dried over $MgSO_4$, filtered, and concentrated. The residue is purified by chromatography on silica gel (50% EtOAc/hexane) to yield 2-[(1-tert-butoxycarbonylamino-cyclopentanecarbonyl)-amino]-3-(4-hydroxy-phenyl)-propionic acid ethyl ester; $^1H$ NMR (250 MHz, $CDCl_3$) δ7.97 (d, 2 H), 6.7 (d, 2 H), 7.51 (d, 1 H), 5.58 (s, 1 H), 4.70–4.80 (m, 2 H), 4.12 (q, 2 H), 3.02 (d, 2 H), 2.07–2.35 (m, 2 H), 1.60–2.00 (m, 6 H), 1.40 (s, 9 H), 1.20 (t, 3H).

1.2 mL of Trifluoromethanesulfonic anhydride (7.1 mmol) is added slowly dropwise to a solution of 2-[(1-tert-butoxycarbonylamino-cyclopentanecarbonyl)-amino]-3-(4-hydroxy-phenyl)-propionic acid ethyl ester (2.70 g, 6.4 mmol) and 0.7 mL (8.7 mmol) of pyridine in 20 mL of $CH_2Cl_2$ at 0° C., and the solution is stirred at 0° C. for 1 hour. The reaction mixture is then partitioned between water and $CH_2Cl_2$. The organic phase is separated and washed with saturated aqueous $NaHCO_3$ solution, dried over $MgSO_4$, filtered, and concentrated to yield 2-[(1-tert-butoxycarbonylamino-cyclopentanecarbonyl)-amino]-3-(4-trifluoromethanesulfonyloxy-phenyl)-propionic acid ethyl ester as a tan solid; $^1H$ NMR (250 MHz, $CDCl_3$) δ7.25 (d, 2 H), 7.17 (d, 2 H), 4.80 (q, 1 H), 4.75 (s, 1 H), 4.10 (two quarters, 2 H), 3.12 (ABX m, 2 H), 2.00–2.20 (m, 2 H), 1.60–2.00 (m, 6 H), 1.40 (s, 9 H), 1.18 (t, 3 H).

Suzuki coupling of 2-[(1-tert-butoxycarbonylamino-cyclopentanecarbonyl)-amino]-3-(4trifluoromethanesulfonyloxphenyl)-propionic acid ethyl ester with p-chlorophenylboronic acid according to a modification of the method reported by Carlson and Shieh (*J. Org. Chem.* 1992, 57, 379) using $PdCl_2$(dppf) as the catalyst, $K_3PO_4$ as base, and DME as solvent, yields 2-[(1-tert-butoxycarbonylamino-cyclopentanecarbonyl)-amino]-3-(4-chlorobiphenyl)-propionic acid ethyl ester.

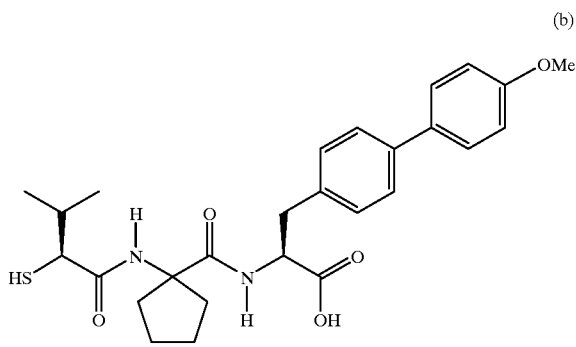

2-{[1-(2-Mercapto-3-methyl-butanoylamino)-cyclopentanecarbonyl]-amino}-3-(4'-methoxy-biphenyl-4-yl)-propionic acid; mp 179–181° C.

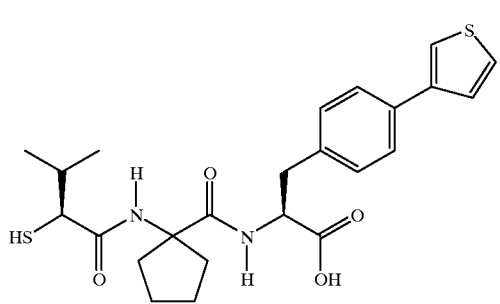

2-{[1-(2-Mercapto-3-methyl-butanoylamino)-cyclopentanecarbonyl]-amino}-3-[4-(thiophen-3-yl)-phenyl]-propionic acid; mp 177–179° C.

2-{[1-(2-Mercapto-3-phenyl-propionylamino)-cyclopentanecarbonyl]-amino}-3-[4-(thiophen-3-yl)-phenyl]-propionic acid; mp 190–192° C.

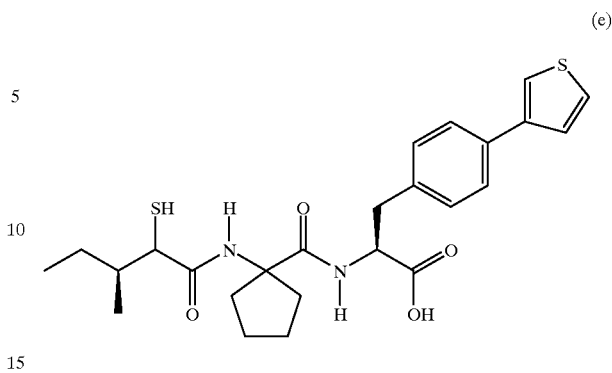

2-{[1-(2-Mercapto-3-methyl-pentanoylamino)-cyclopentanecarbonyl]-amino}-3-[4-(thiophen-3-yl)-phenyl]-propionic acid; mp 99–101° C.

The intermediate, 2-[(tert-butoxycarbonylamino-cyclopentanecarbonyl)-amino]-3-[4-(thiophen-3-yl)-phenyl]-propionic acid ethyl ester is prepared via a Suzuki coupling reaction as follows:

A 25-mL round bottomed flask is charged with 2-{(tert-butoxycarbonylamino-cyclopentanecarbonyl)-amino]-3-(4-trifluoromethanesulfonyloxy-phenyl)-propionic acid ethyl ester (500 mg, 0.905 mmol), thiophen-3-boronic acid (232 mg, 1.81 mmol), PdCl$_2$(dppf) (66 mg, 0.0905 mmol), K$_3$PO$_4$ (768 mg, 3.62 mmol), and 9 mL of THF, and the reaction mixture is heated at reflux for 10 h, and then cooled to room temperature. The reaction mixture is partitioned between EtOAc and water, and the aqueous phase is extracted with EtOAc. The combined organic phases are washed with brine, dried over MgSO$_4$, filtered, and concentrated. The product is purified by chromatography on silica gel (30% EtOAc/Hex).

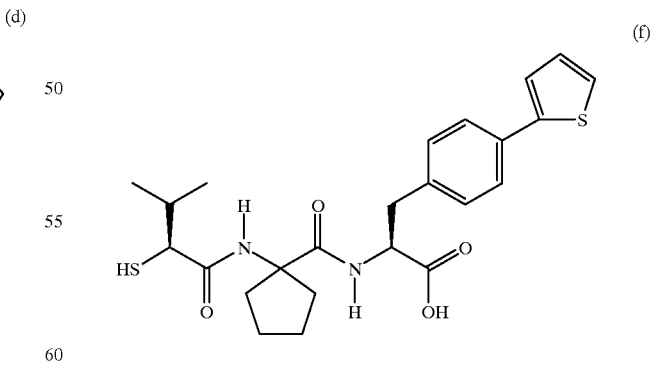

2-{[1-(2-Mercapto-3-methyl-butanoylamino)-cyclopentanecarbonyl]-amino}-3-[4-(thiophen-2-yl)-phenyl]-propionic acid; mp 179–181° C.

(g)

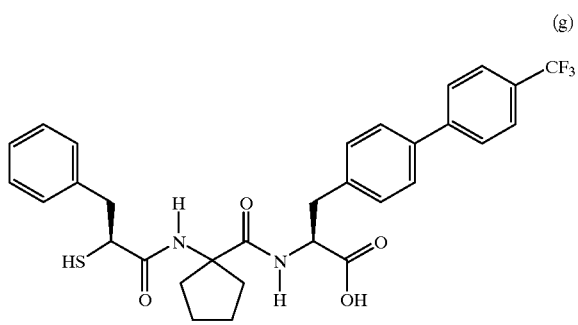

2-{[1-(2-Mercapto-3-phenyl-propionylamino)-cyclopentanecarbonyl]-amino}-3-(4'-trifluoromethyl-biphenyl-4-yl)-propionic acid; mp 222–225° C.

(h)

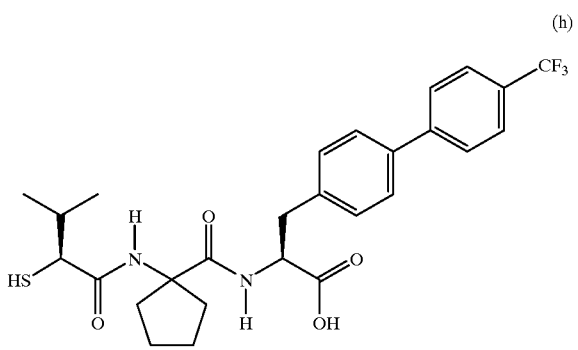

2-{[1-(2-Mercapto-3-methylbutanoylamino)-cyclopentanecarbonyl]-amino}-3-(4'-trifluoromethyl-biphenyl-4-yl)-propionic acid; mp 235–236° C.

(i)

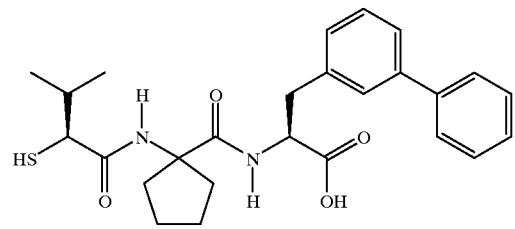

3-Biphenyl-3-yl-2-{[1-(2-mercapto-3-methylbutanoylamino)-cyclopentanecarbonyl]-amino}-propionic acid; mp 75–78° C.

(j)

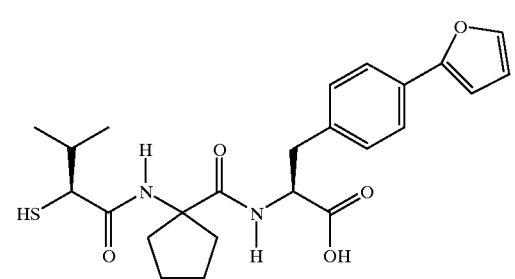

3-[4-(Furan-2-yl)-phenyl]-2-{[1-(2-mercapto-3-methyl-butanoylamino)-cyclopentanecarbonyl]-amino}-propionic acid; mp 152–154° C.

The starting material, 2-[(1-tert-butoxycarbonylamino-cyclopentanecarbonyl)-amino]-3-[4-(furan-2-yl)-phenyl]-propionic acid ethyl ester is prepared from tri-n-butyl-furan-2-yl-stannane as follows:

A 25-mL round bottomed flask is charged with 2-[(tert-butoxycarbonylamino-cyclopentanecarbonyl)-amino]-3-(4-iodo-phenyl)-propionic acid methyl ester (250 mg, 0.48 mmol), tri-n-butyl-furan-2-yl-stannane (196 mg, 0.57 mmol), Pd$_2$(dba)$_3$ (11 mg, 0.012 mmol), triphenylarsine (30 mg, 0.098 mmol), and 10 mL of toluene, and the reaction mixture is heated at reflux overnight, and then cooled to room temperature. The reaction mixture is filtered, diluted with EtOAc and washed with half-saturated aqueous KF. The organic phase is washed with brine, dried over MgSO$_4$, filtered, and concentrated. The product is purified by chromatography on silica gel (30% EtOAc/Hex); mp 107–112° C.

(k)

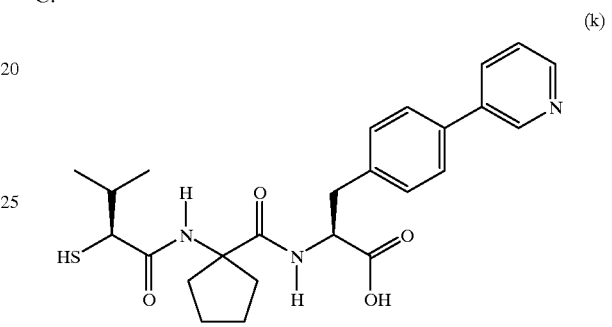

2-{[1-(2-Mercapto-3-methyl-butanoylamino)-cyclopentanecarbonyl]-amino}-3-[4-(pyridin-3-yl)-phenyl]-propionic acid; mp 212–214° C.

(l)

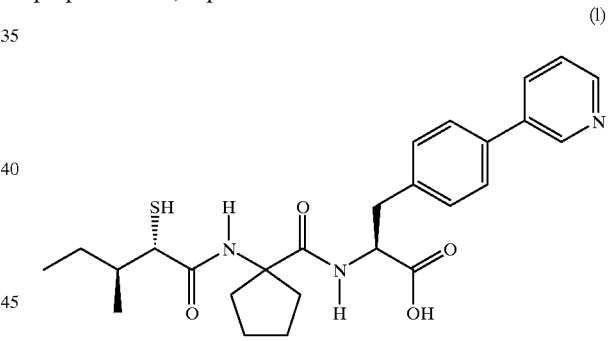

2-{[1-(2-Mercapto-3-methyl-pentanoylamino)-cyclopentanecarbonyl]-amino}-3-[4-(pyridin-3-yl)-phenyl]-propionic acid; mp 207–208° C.

(m)

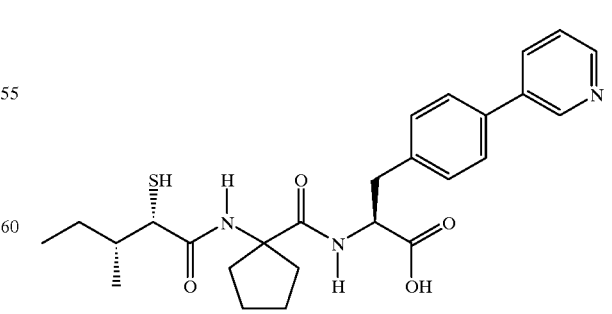

2-{[1-(2-Mercapto-3-methyl-pentanoylamino)-cyclopentanecarbonyl]-amino}-3-[4-(pyridin-3-yl)-phenyl]-propionic acid; mp 205–207° C.

(n)

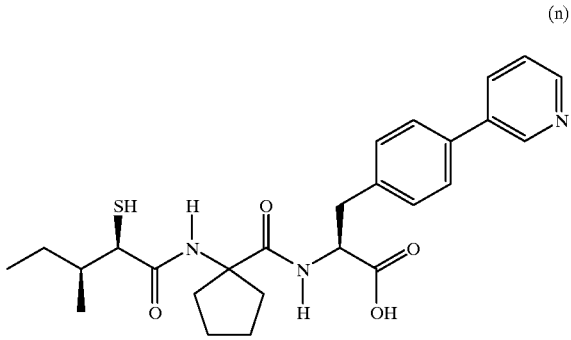

2-{[1-(2-Mercapto-3-methyl-pentanoylamino)-cyclopentanecarbonyl]-amino}-3-[4-(pyridin-3-yl)-phenyl]-propionic acid; mp 210–211° C.;

(o)

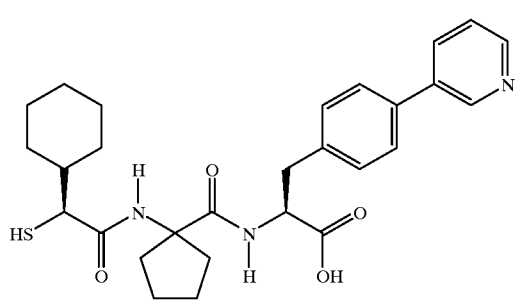

2-{[1-(2-Mercapto-3-cyclohexyl-butanoylamino)-cyclopentanecarbonyl]-amino}-3-[4-(pyridin-3-yl)-phenyl]-propionic acid; mp 243–244° C.

(p)

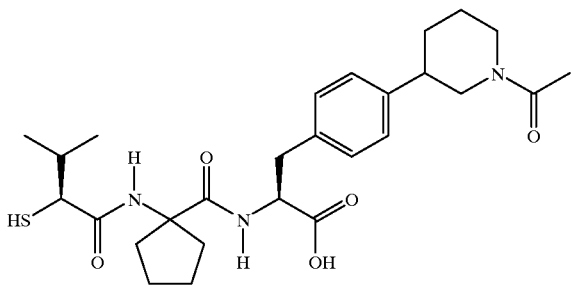

3-[4-(1-Acetyl-piperidin-3-yl)-phenyl]-2-{[1-(2-mercapto-3-methyl-butanoylamino)-cyclopentanecarbonyl]-amino}-propionic acid; mp 190–192° C.

The starting material is prepared as follows:

A suspension of 2-[(1-tert-butoxycarbonylamino-cyclopentanecarbonyl)-amino]-3-{4-(pyridin-3-yl)-phenyl-propionic acid ethyl ester (958 mg) and 10% Pt/C (958 mg) in 10 mL of MeOH is pressurized with $H_2$ at 45 psi and stirred at room temperature for 4 days. The catalyst is filtered off and washed with MeOH. The combined organic phases are concentrated in vacuo. The residue is purified by chromatography on silica gel (EtOAc:MeOH:AcOH 80:20:1) to furnish 2-[(1-tert-butoxycarbonylamino-cyclopentanecarbonyl)-amino]-3-[4-(piperidin-3-yl)-phenyl]-propionic acid ethyl ester; $^1$H NMR (250 MHz, $CDCl_3$) δ7.00–7.10 (m, 4 H), 4.70–4.85 (m, 2 H), 4.10 (q, 2 H), 3.00–3.35 (m, 3 H), 2.60–2.70 (m, 2 H), 2.00–2.30 (m, 4 H), 1.85–2.00 (m, 2 H), 1.50–1.80 (m, 8 H), 1.38 (s, 9 H), 1.16 (t, 3 H).

Acetyl chloride (50 mL, 0.70 mmol) is added slowly to a solution of 2-[(1-tert-butoxycarbonylamino-cyclopentanecarbonyl)-amino]-3-[4-(piperidin-3-yl)-phenyl]-propionic acid ethyl ester (277 mg, 0.57 mmol) and 11 mL (0.79 mmol) of $Et_3N$ in 2 mL of $CH_2Cl_2$. The reaction mixture is stirred at 0° C. for 2 h, and then partitioned between saturated aqueous $NaHCO_3$ solution and $CH_2Cl_2$. The organic phase is washed with brine, dried over $MgSO_4$, filtered, and concentrated. The residue is purified by chromatography on silica gel (EtOAc) to furnish 2-[(1-tert-butoxycarbonylamino-cyclopentanecarbonyl)-amino]-3-[4-(1-acetyl-piperidin-3-yl)-phenyl]-propionic acid ethyl ester; $^1$H NMR (300 MHz, $CDCl_3$) δ7.00–7.15 (m, 4 H), 4.80–4.90 (m, 1 H), 4.70 (br t, 2 H), 4.15 (q, 2 H), 3.00–3.15 (m, 3 H), 2.45–2.70 (m, 2 H), 2.12, 2.08 (s each, 3 H) 1.95–2.40 (m, 6 H), 1.50–1.95 (m, 8 H), 1.40 (s, 9 H), 1.20 (t, 3 H).

EXAMPLE 8
Preparation of α-bromoacylaminocyclopentane-carboxylic Acids and Esters (a)

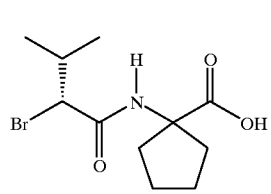

1-(2-Bromo-3-methyl-butanoylamino)-cyclopentanecarboxylic acid is prepared as follows:

5.60 g (18 mmol) of 1-(2-Bromo-3-methyl-butanoylamino)-cyclopentanecarboxylic acid methyl ester is dissolved in 40 mL of MeOH. 37 mL of 1N NaOH is added and the solution is stirred at room temperature for 5 hours. Solvents are removed in vacuo, and the residue is dissolved in water and extracted three times with $Et_2O$. The aqueous phase is acidified with 40 mL of 1N HCl, and the product is filtered off as a white solid; $^1$H NMR (250 MHz, $CD_3OD$) δ7.05 (s, 1 H), 4.15 (d 1 H), 2.15–2.35 (m, 3 H), 1.85–2.00 (m, 2 H), 1.70–1.80 (m, 4 H), 1.00 (d, 3 H), 0.95 (d, 3 H); $[α]_D$+17.87 (10.38 mg/mL in MeOH).

The 1-(2-bromo-3-methyl-butanoylamino)-cyclopentanecarboxylic acid methyl ester precursor is prepared as follows:

4.92 g (27 mmol) of cycloleucine methyl ester hydrochloride and 7.72 (27 mmol) 2-bromo-3-methyl-butanoic acid diisopropylammonium salt are suspended in 50 mL of $CH_2Cl_2$. 3.74 g (27 mmol) of HOAT and 6.20 g (30 mmol) of DCC are added, and the solution is stirred at room temperature overnight. The reaction mixture is filtered, and $CH_2Cl_2$ is removed in vacuo. The residue is taken up in EtOAc, filtered, and washed successively with 1N HCl, water, saturated aqueous $NaHCO_3$ solution, and brine, then dried over $MgSO_4$, filtered, and concentrated. The residue is purified by chromatography on silica gel (30% EtOAc/hexane) to obtain a white solid.; $^1$H NMR (250 MHz, $CD_3OD$) δ6.80 (s, 1 H), 4.25 (d 1 H), 3.70 (s, 3 H), 2.10–2.45 (m, 3 H), 1.85–2.00 (m, 2 H), 1.75–1.85 (m, 4 H), 1.05 (d, 3 H) 0.95 (d, 3 H); $[α]_D$+33.09 (10.35 mg/mL in $CH_2Cl_2$).

The following compounds are similarly prepared.

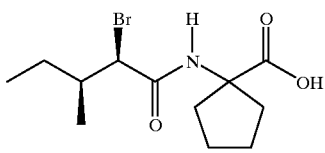
(b)

1-(2-Bromo-3-methyl-pentanoylamino)-cyclopentanecarboxylic acid; White solid; $^1$H NMR (250 MHz, CDCl$_3$) δ7.01 (s, 1 H), 4.89 (br s, 1 H), 4.47 (d, 1 H), 2.21–2.42 (m, 2 H), 1.90–2.20 (m, 3 H), 1.70–1.90 (m, 4 H), 1.30–1.50 (m, 2 H), 0.92 (d, 3 H), 0.90 (t, 3 H); IR (CH$_2$Cl$_2$, cm$^{-1}$) 1713, 1662, 1508, 1190. [α]$_D$+31.759 (10.130 mg/mL in CH$_2$Cl$_2$).

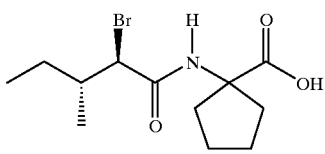
(c)

1-(2-Bromo-3-methyl-pentanoylamino)-cyclopentanecarboxylic acid; White solid; $^1$H NMR (250 MHz, CD$_3$OD) δ4.15 (d, 1 H), 2.20–2.35 (m, 1 H), 2.05–2.15 (m, 1 H), 1.90–2.05 (m, 2 H), 1.70–1.85 (m, 6 H), 1.20–1.45 (m, 1 H), 0.98 (d, 3 H), 0.95 (t, 3 H).

Beispiel 1

EXAMPLE 9

Synthesis of Biaryl Amino Acid Esters

Step 1.

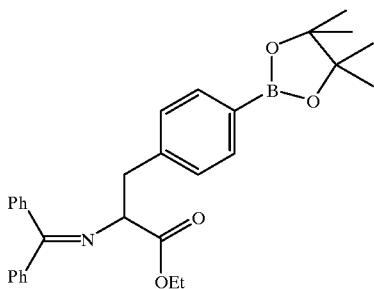

2-(Benzhydrylidene-amino)-3-[4-(4,4,5,5-tetramethyl-[1,3,2]dioxaborolan-2-yl)-phenyl]-propionic acid ethyl ester is prepared via the procedure reported by Stork (*J. Org. Chem.* 1976, 41, 3491), using NaHMDS as the base, from 2-(4-bromomethyl-phenyl)-4,4,5,5-tetramethyl-[1,3,2]dioxaborolane. White solid; mp 120–121° C.; $^1$H NMR (250 MHz, CD$_3$OD) δ7.57 (d, 2 H), 7.27–7.49 (m, 8 H), 7.03 (d, 2 H), 6.58 (d, 2 H), 4.23 (dd, 1 H), 4.18 (q, 2 H), 3.23 (d, 1 H), 3.09 (dd, 1 H), 1.31 (s, 12 H), 1.24 (t, 3 H).

Step 2.

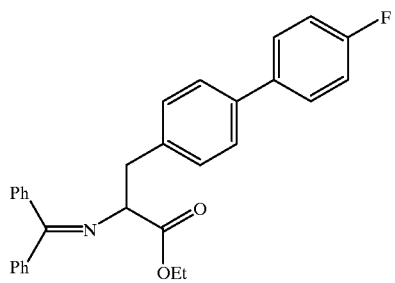

2-(Benzhydrylidene-amino)-3-(4'-fluoro-biphenyl-4-yl)-propionic acid ethyl ester is prepared according to the general procedure reported by Satoh et al. (Tetrahedron Letter Vol. 48, 7645 (1997)). A 50-mL flask is charged with the boronate intermediate of step 1 (600 mg, 1.01 mmol), 1-fluoro-4-iodo-benzene (247 mg, 1.11 mmol), PdCl$_2$(dppf) (37 mg, 0.051 mmol), K$_3$PO$_4$ (860 mg, 4.04 mmol), and 10 mL of DME. The reaction mixture is heated at reflux for 12 hours then cooled to room temperature, and partitioned between EtOAc and water. The organic phase is separated and washed with brine, dried over MgSO$_4$, filtered, and concentrated. The residue is purified by chromatography on silica gel (gradient elution with 5–10% EtOAc/hexane) to furnish the above imine as a light brown oil. $^1$H NMR (300 MHz, CDCl$_3$) δ7.50–7.70 (m, 4 H), 7.25–7.40 (m, 8 H), 7.05–7.20 (m, 4 H), 6.55–6.70 (m, 2 H), 4.15–4.30 (m, 3 H), 3.15–3.35 (m, 2 H), 1.15–1.25 (two t, 3 H).

Step 3.

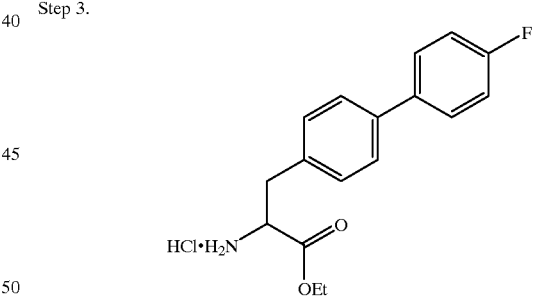

2-Amino-3-(4'-fluoro-biphenyl-4-yl)-propionic acid ethyl ester hydrochloride is prepared as follows:

A 50-mL flask is charged with 2-(benzhydrylidene-amino)-3-(4'-fluoro-biphenyl-4-yl)-propionic acid ethyl ester (350 mg, 0.775 mmol), 10 mL of 1N HCl, and 8 mL of Et$_2$O. The reaction mixture is stirred at room temperature for 12 hours, and then partitioned between ether and water. The aqueous phase is separated and extracted twice with ether, and then concentrated in vacuo to furnish the product as a white solid; $^1$H NMR (250 MHz, CD$_3$OD) δ7.74 (d, 1 H), 7.55–7.65 (m, 4 H), 7.34 (d, 1 H), 7.27 (d, 1 H), 7.17 (t, 1 H), 4.20–4.40 (m, 3 H), 3.15–3.35 (m, 2 H), 1.25 (t, 3 H).

The biaryl substituted amino acid ester starting materials leading to products disclosed in the following examples can be similarly prepared.

EXAMPLE 10

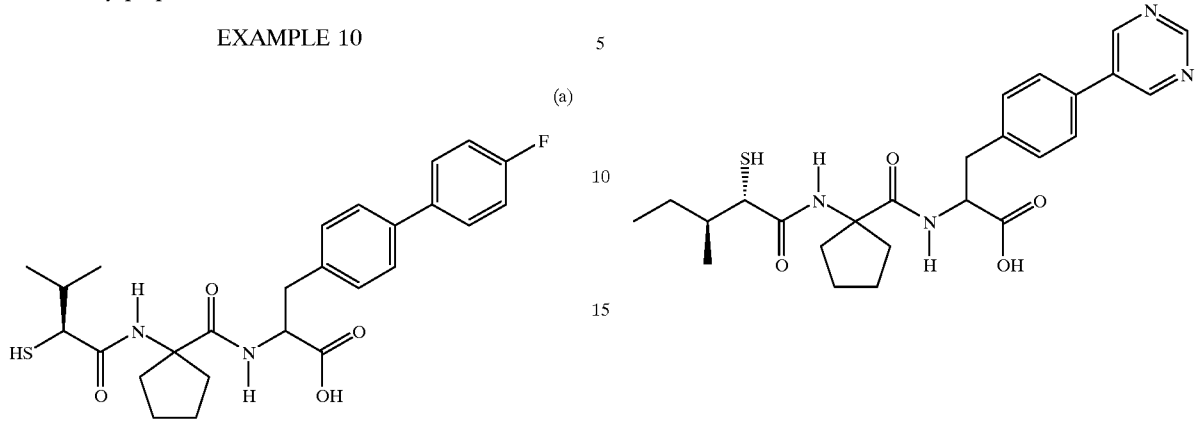

(a)

Condensation of 1-(2-bromo-3-methylbutanoylamino)-cyclopentanecarboxylic acid (Ex. 8) with 2-amino-3(4'-fluorobiphenyl-4-yl)propionic acid ethyl ester hydrochloride (Ex. 9) using DCC, HOAT and triethylamine in methylene chloride yields 3-(4'-fluoro-biphenyl-4-yl)-2-{[1-(2-mercapto-3-methyl-butanoylamino)-cyclopentanecarbonyl]-amino}-propionic acid; mp 196–198° C.

Similarly prepared are:

(b)

2-{[1-(2-Mercapto-3-methyl-butanoylamino)-cyclopentanecarbonyl]-amino}-3-(4-pyridin-2-yl-phenyl-4-yl)-propionic acid (from 2-iodopyridine); mp 199–201° C.

(c)

2-{[1-(2-Mercapto-3-methyl-butanoylamino)-cyclopentanecarbonyl]-amino}-3-(4-pyrimidin-5-yl-phenyl)-propionic acid (from 5-iodopyridine); mp 214–215° C.

(d)

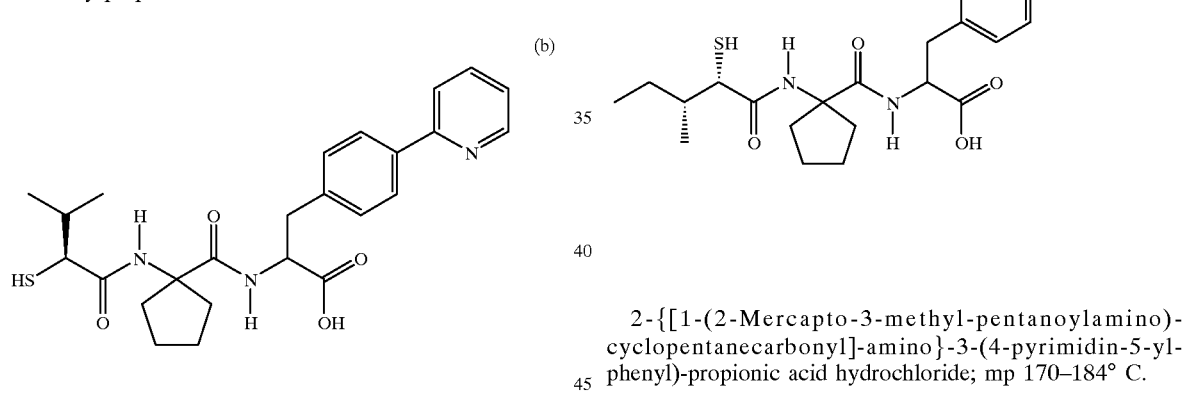

2-{[1-(2-Mercapto-3-methyl-pentanoylamino)-cyclopentanecarbonyl]-amino}-3-(4-pyrimidin-5-yl-phenyl)-propionic acid; mp 206–208° C.

(e)

2-{[1-(2-Mercapto-3-methyl-pentanoylamino)-cyclopentanecarbonyl]-amino}-3-(4-pyrimidin-5-yl-phenyl)-propionic acid hydrochloride; mp 170–184° C.

(f)

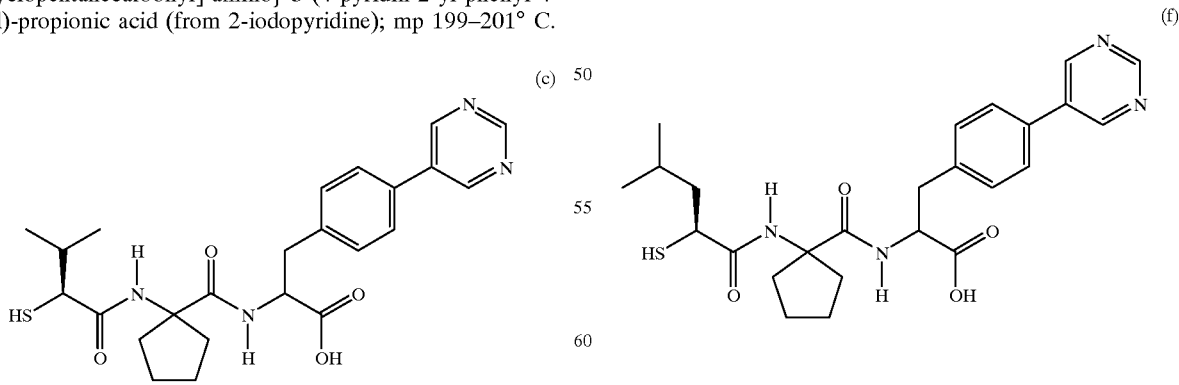

2-{[1-(2-Mercapto-4-methyl-pentanoylamino)-cyclopentanecarbonyl]-amino}-3-(4-pyrimidin-5-yl-phenyl)-propionic acid; mp 192–195° C.

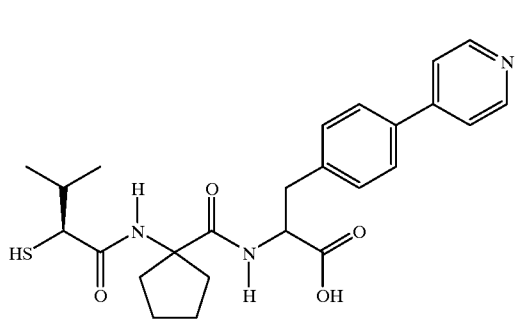

(g)

2-{[1-(2-Mercapto-3-methyl-butanoylamino)-cyclopentanecarbonyl]-amino}-3-(4-yl-phenyl)-propionic acid (from 4-bromoyridine); mp 236–238° C.

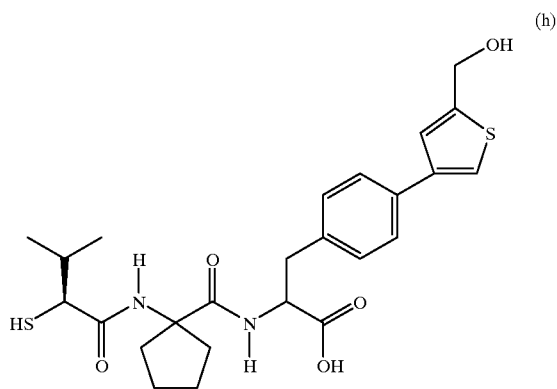

(h)

3-[4-(5-Hydroxymethyl-thiophen-3-yl)-phenyl]-2-{[1-(2-mercapto-3-methyl-butanoylamino)-cyclopentanecarbonyl]-amino}-propionic acid (starting from 4-bromo-2-thiophenecarboxaldehyde); mp 155–158° C.

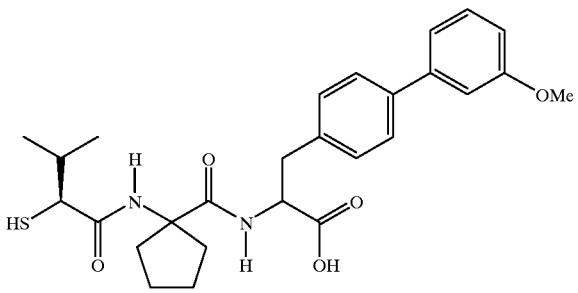

(i)

2-{[1-(2-Mercapto-3-methyl-butanoylamino)-cyclopentanecarbonyl]-amino}-3-(3'-methoxy-biphenyl-4-yl)-propionic acid (from 1-iodo-3-methoxybenze); mp 159–160° C.

(j)

3-(2',3'-Dimethoxy-biphenyl-4-yl)-2-{[1-(2-mercapto-3-methyl-butanoylamino)-cyclopentanecarbonyl]-amino}-propionic acid (from 1-trifluoromethylsulfonyloxy-2,3-dimethoxy-benzene); mp 83–86° C.

(k)

3-(3',5'-Dimethoxy-biphenyl-4-yl)-2-{[1-(2-mercapto-3-methyl-butanoylamino)-cyclopentanecarbonyl]-amino}-propionic acid; mp 150–152° C.

EXAMPLE 11

Prepared similarly to procedures previously described are:

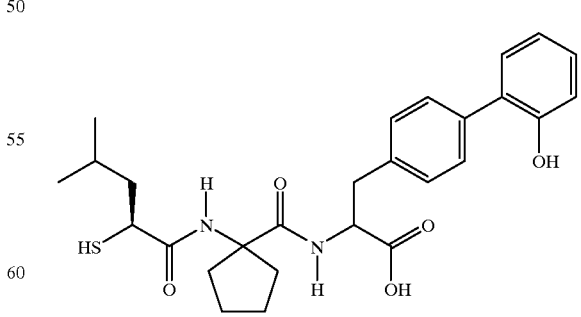

(a)

3-(2'-Hydroxy-biphenyl-4-yl)-2-{[1-(2-mercapto-4-methyl-pentanoylamino)-cyclopentanecarbonyl]-amino}-propionic acid; mp 215–217° C.

The starting material is prepared as follows:

The Boc-protected boronophenylalanine reagent, 2-(N-t-Boc-amino)-3-[4-(4,4,5,5-tetramethyl-[1,3,2]dioxaborolan-2-yl)-phenyl]propionic acid ethyl ester (see Roberts et al., Tetrahedron Letters 1980, 21, 3435) is condensed with 1-acetoxy-2-iodobenzene in the Suzuki coupling reaction followed by coupling to N-t-Boc-cycloleucine methyl ester to obtain the intermediate

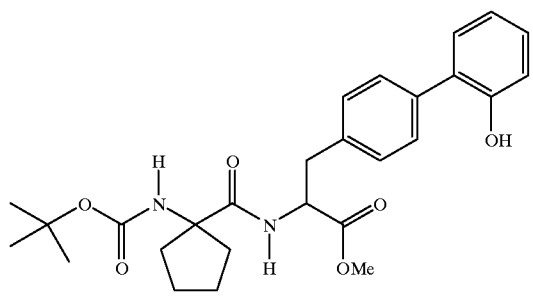

2-[(1-tert-butoxycarbonylamino-cyclopentanecarbonyl)-amino]-3-(2'-hydroxy-biphenyl-4-yl)-propionic acid methyl ester; $^1$H NMR (300 MHz, CD$_3$OD) δ7.40 (d, 2 H), 7.20–7.26 (m, 4 H), 6.94–6.99 (m, 2 H), 5.79 (br s, 1 H), 4.88 (br q, 1 H), 4.78 (s, 1 H), 3.73 (s, 3 H), 3.01–3.24 (m, 2 H), 2.10–2.35 (m, 2 H), 1.55–2.00 (m, 6 H), 1.40 (s, 9 H).

(b)

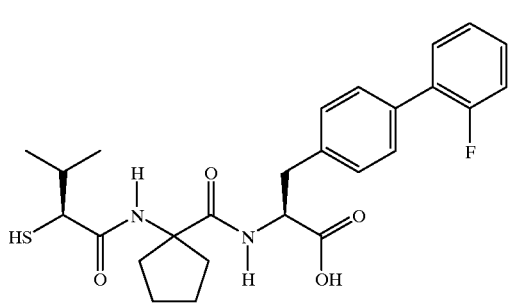

3-(2'-Fluoro-biphenyl-4-yl)-2-{[1-(2-mercapto-3-methyl-butanoylamino)-cyclopentanecarbonyl]-amino}-propionic acid (from 1-fluoro-2-iodobenzene); mp 171–173° C.

(c)

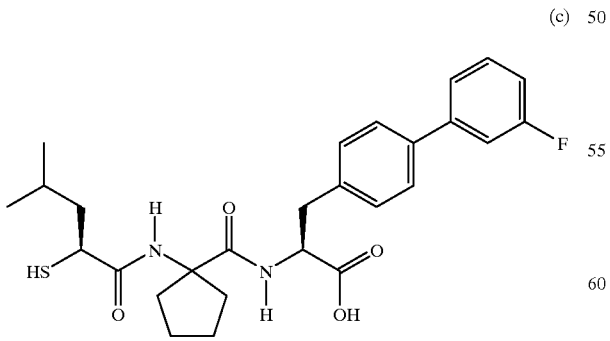

3-(3'-Fluoro-biphenyl-4-yl)-2-{[1-(2-mercapto-4-methyl-pentanoylamino)-cyclopentanecarbonyl]-amino}-propionic acid (from 1-fluoro-3-iodobenzene); mp 125–128° C.

EXAMPLE 12

Prepared similarly to procedures previously described are:

(a)

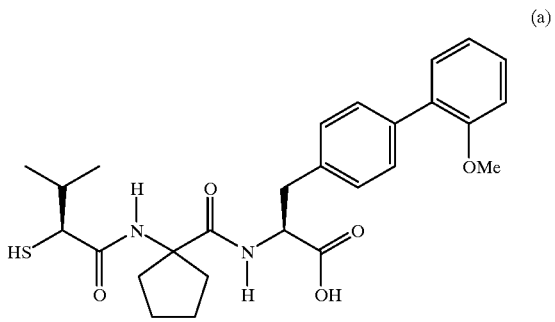

2-{[1-(2-Mercapto-3-methyl-butanoylamino)-cyclopentanecarbonyl]-amino}-3-(2'-methoxy-biphenyl-4-yl)-propionic acid; mp 172–174° C.

The starting material of the formula

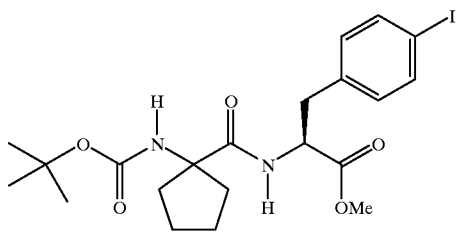

namely, 2-[(1-tert-butoxycarbonylamino-cyclopentatecarbonyl)-amino]-3-(4-iodo-phenyl)-propionic acid methyl ester, is prepared by standard coupling of N-Boc cycloleucine and 4-iodo-phenylalanine methyl ester under conditions previously described (DCC, HOAT, Et$_3$N); mp 137° C.

This is condensed with 2-methoxyphenylboronic acid to yield the intermediate of the formula

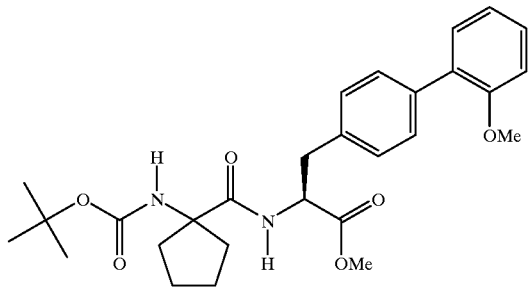

namely, 2-[(1-tert-butoxycarbonylamino)-cyclopentanecarbonyl)-amino]-3-(2'-methoxy-biphenyl-4-yl)-propionic acid methyl ester; $^1$H NMR (250 MHz, CDCl$_3$) δ7.45 (d, 2 H), 7.28 (d, 1 H), 7.15 (d, 2 H), 6.85–7.08 (m, 3 H), 5.74 (s, 1 H), 4.88 (app q, 1 H), 4.74 (br s, 1 H), 3.78 (s, 3 H), 3.69 (s, 3 H), 3.00–3.20 (ABX m, 2 H), 1.60–2.40 (m, 8 H), 1.40 (s, 9 H).

(b)

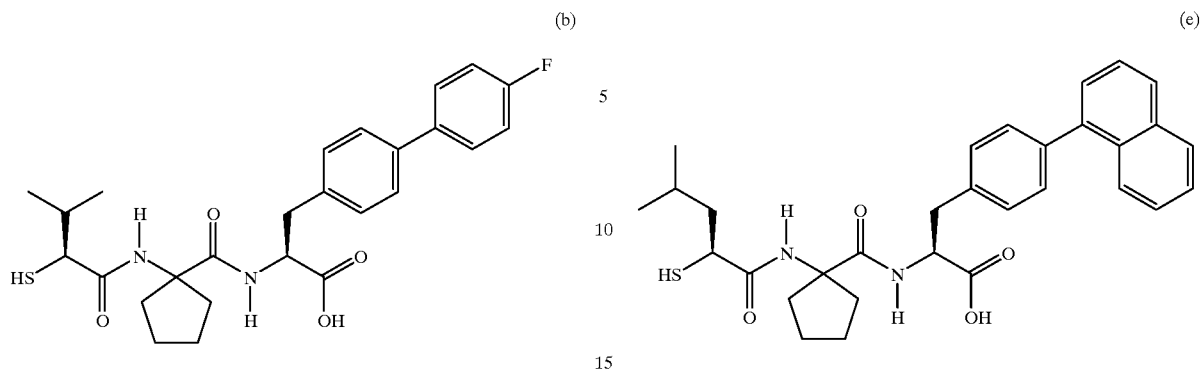

3-(4'-Fluoro-biphenyl-4-yl)-2-{[1-(2-mercapto-3-methyl-butanoylamino)-cyclopentanecarbonyl]-amino}-propionic acid (from 4-fluorophenyl-boronic acid); mp 106–108° C.

(c)

3-methyl-butanoylamino)-cyclopentanecarbonyl]-amino}-propionic acid (from 3-chloro-4-fluorophenyl-boronic acid); mp 170–172° C.

2-{[1-(2-Mercapto-3-methyl-butanoylamino)-cyclopentanecarbonyl]-amino}-3-(3'-trifluoromethyl-biphenyl-4-yl)-propionic acid (from 4-trifluoromethylphenylboronic acid); mp 190–192° C.

(d)

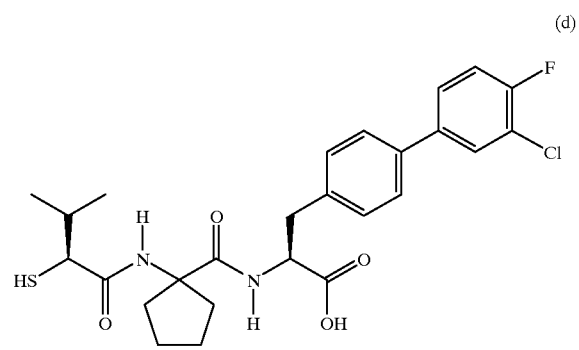

3-(3'-Chloro-4'-fluoro-biphenyl-4-yl)-2-{[1-(2-mercapto- (e)

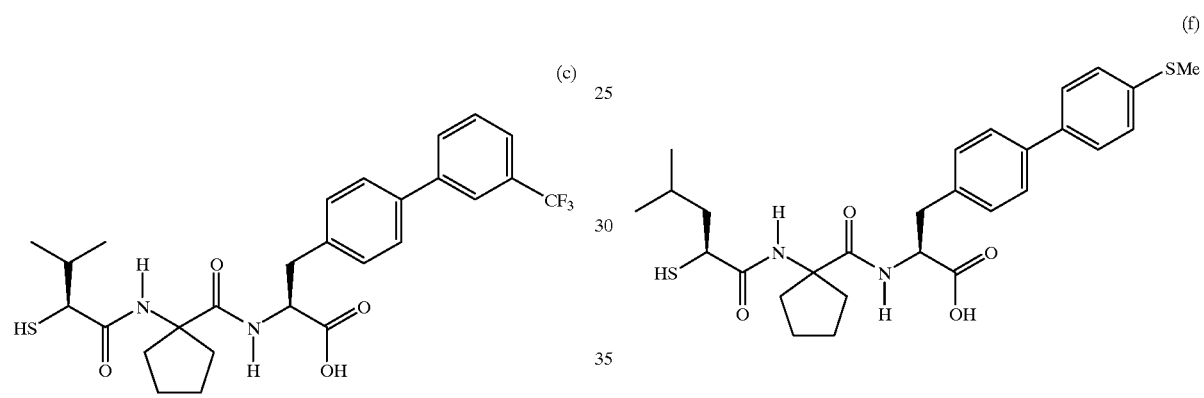

2-{[1-(2-Mercapto-4-methyl-pentanoylamino)-cyclopentanecarbonyl]-amino}-3-(4'-naphthalen-1-yl-biphenyl-4-yl)-propionic acid (from naphthalen-1-yl-boronic acid); mp 151–154° C.

(f)

2-{[1-(2-mercapto4-methyl-pentanoylamino)-cyclopentanecarbonyl]-amino}-3-(4'-methylthio-biphenyl-4-yl)-propionic acid (from 4-methylthiophenyl-boronic acid; mp 187–189° C.

EXAMPLE 13

Prepared similarly to procedures previously described are also:

(a) 2-{[1-(2-Mercapto-4-methyl-pentanoylamino)-cyclopentanecarbonyl]-amino}-3-(4,5,6,7-tetrafluoro-3-methyl-benzofuran-2-yl)-propionic acid; mp 115–117° C.

The starting material, 2-amino-3-(4,5,6,7-tetrafluoro-3-methyl-benzofuran-2-yl)-propionic acid methyl ester hydrochloride is prepared according to the procedure reported by Stork et al (J. Org. Chem. 1976, 41, 3491) using NaHMDS as the base, from 2bromomethyl-4,5,6,7-tetrafluro-3-methyl-benzofuran (prepared from the reduction of the corresponding ethyl ester and conversion of the resulting alcohol to the bromide); $^1$H NMR (300 MHz, CD$_3$OD) δ4.75 (dd, 1 H), 3.70 (s, 3 H), 3.25 (dd, 1 H), 3.10 (dd, 1 H), 2.40 (s, 3 H).

(b) 3-(1H-Indol-3-yl)-2-{[1-(2-mercapto-4-methyl-pentanoylamino)-cyclopentanecarbonyl]-amino}-propionic acid; mp 116–118° C.

(c) 3-(1H-Indol-3-yl)-2-{[1-(2-mercapto-pentanoylamino)-cyclopentanecarbonyl]-amino}-propionic acid; mp 102–105° C.

(d) 2-({1-[3-(4-Hydroxyphenyl)-2-mercaptopropionylamino]-cyclopentanecarbonyl}-amino)-3-(1H-indol-3-yl)-propionic acid; $^1$H NMR (300 MHz, CD$_3$OD) δ7.53 (dd, 1 H), 7.25 (dd, 1 H), 6.90–7.10 (m, 5 H), 6.58–6.70 (m, 2 H), 4.60–4.70 (m, 1 H), 3.40–3.50 (m, 1 H), 3.15–3.35 (m, 2 H), 2.80–3.02 (m, 1 H), 2.72–2.80 (m, 1 H), 1.45–2.18 (m, 8 H).

(e) 3-Benzo[b]thiophen-3-yl-2-{[1-(2-mercapto4-methylpentanoylamino)-cyclopentanecarbonyl]-amino}-propionic acid; mp 135–137° C.

(f) 3-(1H-Indol-3-yl)-2-{[1-(2-mercapto-3-methylbutanoylamino)-cyclopentanecarbonyl]-amino}-propionic acid.

(g) 3-(1H-Indolyl-3-yl)-2-{[1-(2-acetylthio-3-methylbutanoylamino)-cyclopentanecarbonyl]-amino}-propionic acid n-butyl ester; m.p. 111–112° C.

(h) 3-(4-Biphenylyl)-2-{[1-(2-mercapto-3-methylbutanoylamino)-cyclopentanecarbonyl]amino}-propionic acid; m.p. 180–181° C.

What is claimed is:

1. A method of inhibiting endothelin converting enzyme in a mammal which comprises administering to a mammal in need thereof an effective endothelin converting enzyme inhibiting amount of a compound of the formula.

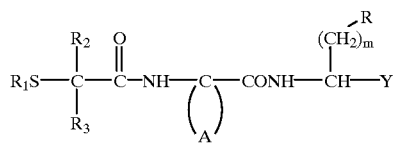

(I)

wherein

R represents bicyclic carbocyclic aryl or bicyclic heterocyclic aryl; or a wholly or partially saturated form thereof; or R represents monocyclic carbocyclic aryl substituted by carbocyclic aryl or by heterocyclic aryl; or R represents monocyclic carbocyclic aryl substituted by cycloalkyl; or R represents monocyclic carbocyclic aryl substituted by azacycloalkyl which is optionally substituted by lower alkyl or acyl; or R represents cycloalkyl substituted by cycloalkyl or azacycloalkyl;

R$_1$ represents hydrogen or acyl;

R$_2$ represents hydrogen, lower alkyl, carbocyclic or heterocyclic aryl, carbocyclic or heterocyclic aryl-lower alkyl, cycloalkyl, cycloalkyl-lower alkyl, biaryl, biaryl-lower alkyl, (hydroxy, lower alkoxy or acyloxy)-lower alkyl, or lower alkyl-(thio, sulfinyl or sulfonyl)-lower alkyl;

R$_3$ represents hydrogen or lower alkyl; or R$_2$ and R$_3$ together with the carbon atom to which they are attached represent cycloalkylidene or benzo-fused cycloalkylidene;

A together with the carbon atom to which it is attached forms a ring and represents 3 to 10 membered cycloalkylidene or 5 to 10 membered cycloalkenylidene radical which may be substituted by lower alkyl or aryl-lower alkyl or may be fused to a saturated or unsaturated carbocyclic 5–7-membered ring; or A together with the carbon to which it is attached represents 5 to 6 membered oxacycloalkylidene, thiacycloalkylidene or azacycloalkylidene optionally substituted by lower alkyl or aryl-lower alkyl; or A together with the carbon atom to which it is attached represents 2,2-norbonylidene;

m is zero or 1–3;

Y represents 5-tetrazolyl, carboxyl or carboxyl derivatized in form of a pharmaceutically acceptable ester;

a disulfide derivative derived from a said compound wherein R$_1$ is hydrogen; or a pharmaceutically acceptable salt thereof.

2. A method according to claim 1 wherein the asymmetric carbon with the substituent Y has the S-configuration.

3. A method according to claim 1 which comprises the administration of a compound of the formula

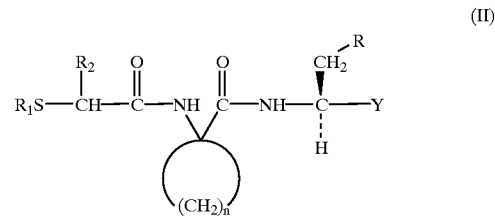

(II)

wherein R represents benzothiophenyl, naphthyl, benzofuranyl, indolyl, or monocyclic carbocyclic aryl substituted by monocyclic carbocyclic aryl or by monocyclic heterocyclic aryl; R$_1$ represents hydrogen or carboxyl derived acyl; R$_2$ represents lower alkyl, hydroxy lower alkyl, (lower alkylthio- or lower alkoxy-)lower alkyl, carbocyclic or heterocyclic aryl, carbocyclic or heterocyclic aryl-lower alkyl, cycloalkyl, cycloalkyl-lower alkyl, or biaryl-lower alkyl; Y represents 5-tetrazolyl, carboxyl or carboxyl derivatized in form of a pharmaceutically acceptable ester; n represents 2–6; a disulfide derivative derived from said compounds wherein R$_1$ is hydrogen; or a pharmaceutically acceptable salt thereof.

4. A method according to claim 3 wherein R has meaning as defined in said claim; R$_1$ represents hydrogen, aryl-lower alkanoyl, lower alkanoyl, lower alkoxy-lower alkanoyl, or heterocyclic or carbocyclic aroyl; R$_2$ represents C$_2$–C$_4$ alkyl interrupted by S or O, C$_2$–C$_5$-alkyl or cyclohexyl; Y represents 5-tetrazolyl, carboxyl, lower alkoxycarbonyl, carbocyclic or heterocyclic aryl-lower alkoxycarbonyl, α-(lower alkanoyloxy-, lower alkoxycarbonyl- or di-lower alkylaminocarbonyl-)lower alkoxycarbonyl; n is 2, 4 or 5; or a pharmaceutically acceptable salts thereof.

5. A method according to claim 3 which comprises the administration of a compound of the formula

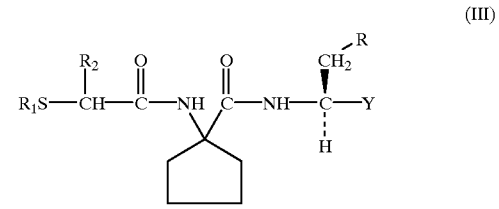

(III)

or of the formula

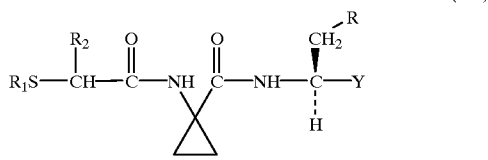

wherein
R represents benzothiophenyl, naphthyl, benzofuranyl, indolyl, or monocyclic carbocyclic aryl substituted by monocyclic carbocyclic aryl or by monocyclic heterocyclic aryl;

$R_1$ represents hydrogen, lower alkanoyl, methoxy-lower alkanoyl, benzoyl or pyridylcarbonyl;

$R_2$ represents $C_2-C_5$-alkyl, cyclohexyl or $C_2-C_4$-alkyl interrupted by O or S;

Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

6. A method according to claim 5 which comprises the administration of a compound of formula III or a pharmaceutically acceptable salt thereof.

7. A method according to claim 1 which comprises the administration of a compound of the formula

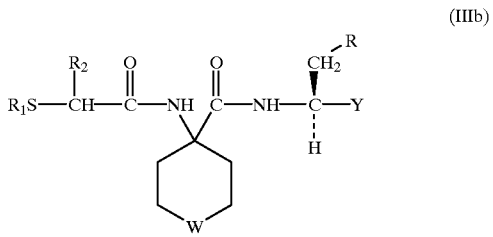

wherein
R represents benzothiophenyl, naphthyl, benzofuranyl, indolyl or monocarbocyclic aryl substituted by monocyclic carbocyclic aryl or by monocyclic heterocyclic aryl;

W represents $CH_2$, O, S or $NR_4$ in which $R_4$ is hydrogen, acyl, lower alkyl or aryl-lower alkyl;

$R_1$ represents hydrogen, lower alkanoyl, methoxy-lower alkanoyl, benzoyl or pyridylcarbonyl;

$R_2$ represents $C_2-C_5$-alkyl, cyclohexyl or $C_2-C_4$-alkyl interrupted by O or S;

Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

8. A method according to claim 3 wherein R represents 4-biphenylyl or 3-indolyl; $R_1$ represents hydrogen or lower alkanoyl; $R_2$ represents $C_3-C_5$-alkyl, Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

9. A method according to claim 3 wherein R represents 4-biphenylyl; $R_1$ represents hydrogen or lower alkanoyl; $R_2$ represents n-propyl, n-butyl or isobutyl; and Y represents 5-tetrazolyl, carboxyl or lower alkoxycarbonyl; or a pharmaceutically acceptable salt thereof.

10. A method according to claim 6 wherein R represents 4-biphenylyl; $R_1$ represents hydrogen or lower alkanoyl; $R_2$ represents n-propyl, n-butyl or isobutyl; and Y represents 5-tetrazolyl, carboxyl or lower alkoxycarbonyl; or a pharmaceutically acceptable salt thereof.

11. A method according to claim 6 wherein Y represents 5-tetrazolyl, carboxyl or lower alkoxycarbonyl; $R_1$ represents hydrogen or lower alkanoyl; $R_2$ represents n-propyl, n-butyl, isobutyl, n-pentyl, methoxyethyl or methylthioethyl; and R represents 3-indolyl, 4-(5-isoxazolyl)-phenyl, 4-(2- or 3-furanyl)-phenyl, 4-(2- or 3-thienyl)-phenyl, 4-biphenylyl, 4-(2- or 3-pyridyl)-phenyl, 4-(5-pyrimidinyl)-phenyl, or 4-biphenylyl substituted on one or both benzene rings by lower alkyl, lower alkoxy, hydroxy, lower alkylthio, halogen or trifluoromethyl; or a pharmaceutically acceptable salt thereof.

12. A method according to claim 6 which comprises the administration of a compound selected from the group consisting of a compound of formula III, (i) wherein Y is carboxyl, $R_1$ is hydrogen, $R_2$ is n-propyl and R is 4-biphenylyl, or a pharmaceutically acceptable salt thereof; (ii) wherein Y is methoxycarbonyl, $R_1$ is acetyl, $R_2$ is n-propyl and R is 4-biphenylyl; (iii) wherein Y is carboxyl, $R_1$ is hydrogen, $R_2$ is isobutyl and R is 3-indolyl, or a pharmaceutically acceptable salt thereof; and (iv) wherein Y is methoxycarbonyl, $R_1$ is acetyl, $R_2$ is isobutyl and R is 3-indolyl.

13. A method according to claim 6 wherein R is 4-biphenylyl or 3-indolyl; and $R_2$ is isopropyl.

14. A method according to claim 13 wherein Y is ethoxycarbonyl, $R_1$ is 2-methoxyacetyl, $R_2$ is isopropyl, and R is 3-indolyl.

15. A method according to claim 13 wherein Y is carboxyl, $R_1$ is hydrogen, $R_2$ is isopropyl and R is 3-indolyl.

16. A method of treating endothelin-dependent disorders selected from cerebral vasospasm, stroke, bronchial asthma, complications associated with organ transplantation and erectile dysfunction in a mammal which comprises administering to a mammal in need thereof an effective amount of a compound of the formula

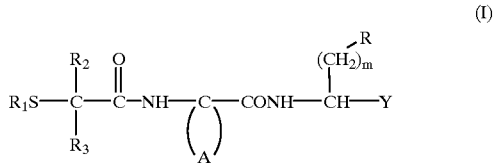

wherein
R represents bicyclic carbocyclic aryl or bicyclic heterocyclic aryl; or a wholly or partially saturated form thereof; or R represents monocyclic carbocyclic aryl substituted by carbocyclic aryl or by heterocyclic aryl; or R represents monocyclic carbocyclic aryl substituted by cycloalkyl; or R represents monocyclic carbocyclic aryl substituted by azacycloalkyl which is optionally substituted by lower alkyl or acyl; or R represents cycloalkyl substituted by cycloalkyl or azacycloalkyl;

$R_1$ represents hydrogen or acyl;

$R_2$ represents hydrogen, lower alkyl, carbocyclic or heterocyclic aryl, carbocyclic or heterocyclic aryl-lower alkyl, cycloalkyl, cycloalkyl-lower alkyl, biaryl, biaryl-lower alkyl, (hydroxy, lower alkoxy or acyloxy)-lower alkyl, or lower alkyl-(thio, sulfinyl or sulfonyl)-lower alkyl;

$R_3$ represents hydrogen or lower alkyl; or $R_2$ and $R_3$ together with the carbon atom to which they are attached represent cycloalkylidene or benzo-fused cycloalkylidene;

A together with the carbon atom to which it is attached forms a ring and represents 3 to 10 membered cycloalkylidene or 5 to 10 membered cycloalkenylidene radical which may be substituted by lower alkyl or aryl-lower alkyl or may be fused to a saturated or unsaturated carbocyclic 5–7-membered ring; or A together with the carbon to which it is attached represents 5 to 6 membered oxacycloalkylidene, thiacycloalkylidene or azacycloalkylidene optionally substituted by lower alkyl or aryl-lower alkyl; or A together with the carbon atom to which it is attached represents 2,2-norbonylidene;

m is zero or 1–3;

Y represents 5-tetrazolyl, carboxyl or carboxyl derivatized in form of a pharmaceutically acceptable ester;

a disulfide derivative derived from a said compound wherein $R_1$ is hydrogen; or a pharmaceutically acceptable salt thereof.

17. A method according to claim 16 which comprises administering a compound of the formula

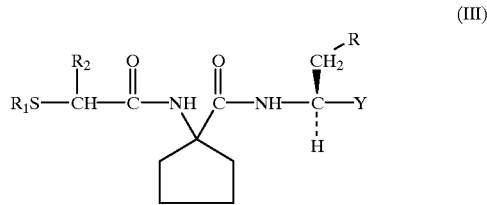

(III)

wherein R represents benzothiophenyl, naphthyl, benzofuranyl, indolyl, or monocyclic carbocyclic aryl substituted by monocyclic carbocyclic aryl or by monocyclic heterocyclic aryl; $R_1$ represents hydrogen, lower alkanoyl, methoxy-lower alkanoyl, benzoyl or pyridylcarbonyl; $R_2$ represents $C_2$–$C_5$-alkyl, cyclohexyl or $C_2$–$C_4$-alkyl interrupted by O or S; Y represents 5-tetrazolyl, carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; or a pharmaceutically acceptable salt thereof.

* * * * *